United States Patent
Shir et al.

(10) Patent No.: US 7,927,792 B2
(45) Date of Patent: Apr. 19, 2011

(54) TARGETED DOUBLE STRANDED RNA MEDIATED CELL KILLING

(75) Inventors: Alexei Shir, Jerusalem (IL); Alexander Levitzki, Jerusalem (IL)

(73) Assignee: Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 135 days.

(21) Appl. No.: 10/535,189

(22) PCT Filed: Nov. 12, 2003

(86) PCT No.: PCT/IL03/00957
§ 371 (c)(1),
(2), (4) Date: Sep. 21, 2006

(87) PCT Pub. No.: WO2004/045491
PCT Pub. Date: Jun. 3, 2004

(65) Prior Publication Data
US 2007/0010467 A1   Jan. 11, 2007

Related U.S. Application Data

(60) Provisional application No. 60/426,876, filed on Nov. 18, 2002.

(51) Int. Cl.
*C12Q 1/68* (2006.01)
*C12P 19/34* (2006.01)
*C12N 5/00* (2006.01)
*C12N 5/02* (2006.01)
*A01N 43/04* (2006.01)

(52) U.S. Cl. ........... 435/6; 435/91.1; 435/325; 435/375; 514/44

(58) Field of Classification Search .................. 536/23.1, 536/24.3, 24.33, 24.5; 435/6, 325, 375, 91.1; 514/44
See application file for complete search history.

(56) References Cited

FOREIGN PATENT DOCUMENTS

| WO | WO 94/23050 | 10/1994 |
|---|---|---|
| WO | WO 01/43777 | 6/2001 |
| WO | WO 03/078576 | 9/2003 |

OTHER PUBLICATIONS

Abounader et al. The in vivo targeting of scatter factor/hepatocyte growth factor and c-met expression via U1snRNA/ribozymes inhibits glioma growth and angiogenesis and promotes apoptosis. The FASEB Journal, Jan. 2002;16(1):108-10. Epub Nov. 29, 2001.*
Czubayko et al. Melanoma angiogenesis and metastasis is modulated by a ribozyme targeted to the secreted growth factor pleiotrophin. Proc. Natl. Acad. Sci., 1996 vol. 93:14753-14758.*
Zhao et al. Selective disruption of neuregulin-1 function in vertebrate embryos using ribozyme-tRNA transgenes. Development, 1998 vol. 125:1899-1907.*
Yamazaki et al. (Journal of the National Cancer Institute, 1998 vol. 90:581-587).*
Ogris et al. (Journal of Biological Chemistry, 2001 vol. 276:47550-47555).*

(Continued)

*Primary Examiner* — Sean McGarry
*Assistant Examiner* — Terra Cotta Gibbs

(57) ABSTRACT

A method of killing a specific target cell/tissue is disclosed. The method comprises exposing the specific target cell/tissue to a composition-of-matter comprising a double stranded RNA molecule associated with a targeting moiety selected capable of targeting to the specific target cell/tissue, thereby killing the specific target cell/tissue.

11 Claims, 11 Drawing Sheets

OTHER PUBLICATIONS

Shir et al. EGF-Receptor-Targeted Synthetic Double-Stranded RNA Eliminates Glioblastoma, Breast Cancer, and Adenocarcinoma Tumors in Mice. PLOS Medicine, 2006 vol. 3, No. 1:0125-0135.*

Ogris et al. "DNA/Polyethylenimine Transfection Particles: Influence of Ligands, Polymer Size, and PEGylation on Internatlization and Gene Expression", AAPS PharmSci 3(3): Article 21: 1-11, 2001.

Sosnowski et al. "Targeting DNA to Cells with Basic Fibroblast Growth Factor (FGF2)", Journal of Biological Chemistry 271(52): 33647-33653, 1996.

Xu et al. "The Contribution of Poly-L-Lysine, Epidermal Growth Factor and Streptavidin to EGF/PLL/DNA Polyplex Formation", Gene Therapy 5: 1235-1243, 1998.

Shir et al. "Efficient Killing of Glioblastoma and Other Cancers by Cancer Specific Transfection of dsRNA".

Shir et al. "Inhibition of Glioma Growth by Tumor-Specific Activation of Double-Stranded RNA-Dependent Protein Kinase PKR", Nature Biotechnology 20(9): 895-900, 2002. Abstract.

Merdan et al. "Prospects for Cationic Polymers in Gene and Oligonucleotide Therapy Against Cancer", Advanced Drug Delivery Reviews, 54(5): 715-758, 2002.

Blessing et al. "Different Strategies for Formation of PEGylated EGF-Conjugated PEI/DNA Complexes for Targeted Gene Delivery", Bioconjugate Chemistry, 12(4): 529-537, 2001, Abstract.

Bettinger et al. "Peptide-Mediated RNA Delivery: A Novel Approach for Enhanced Transfection of Primary and Post-Mitotic Cells", Nucleic Acids Research, 29(18): 3882-3891, 2001. Abstract.

Liu et al. "Double-Stranded Ribonucleic Acid (RNA) Induces β-Cell Fas Messenger RNA Expression and Increases Cytokine-Induced β-Cell Apoptosis", Endocrinology, 142(6): 2593-2599, 2001. Abstract.

Shir et al. "EGF Receptor-Targeted Synthetic Double-Stranded RNA Eliminates Glioblastoma, Breast Cancer, and Adenocarcinoma Tumors in Mice", PLoS Medicine, 3(1/e6): 0125-0135, 2006.

Bansal et al. "Gene Therapy for Brain Tumors", Current Oncology Reports, 2: 463-472, 2000.

Bukrinsky et al. "A Nuclear Localization Signal Within HIV-1 Matrix Protein That Governs Infection of Non-Diving Cells", Nature, 365: 666-669, 1993.

Eriksdotter Joenhagen "Intracerebroventricular Infusion of Nerve Growth Factor in Three Patients With Alzheimer's Disease", Dementia and Geriatric Cognitive Disorders, 9: 246-257, 1998.

Farrell et al. "Interferon Action:Two Distinct Pathways for Inhibition of Protein Synthesis by Double-Stranded RNA", Proc. Natl. Acad. Sci. USA, 75(12): 5893-5897, 1978.

Gallay et al. "HIV Nuclear Import Is Governed by the Phosphotyrosine-Mediated Binding of Matrix to the Core Domain of Integrase", Cell, 83: 569-576, 1995.

George "Platelet-Derived Growth Factor Receptors: A Therapeutic Target in Solid Tumors", Seminars in Oncology, 28(5/Suppl.17): 27-33, 2001.

Giles "The Vascular Endothelial Growth Factor (VEGF) Signaling Pathway: A Therapeutic Target in Patients With Hematologic Malignancies", The Oncologist, 6(Suppl.5): 32-39, 2001.

Iordanov et al. "Activation of P38 Mitogen-Activated Protein Kinase and C-Jun NH2-Terminal Kinase by Double-Stranded RNA and Encephalomyocarditis Virus: Involvement of RNase L, Protein Kinase R, and Alternative Pathways", Molecular and Cellular Biology, 20(2): 617-627, 2000.

Jagus et al. "PKR, Apoptosis and Cancer", The Inernational Journal of Biochemistry & Cell Biology, 31: 123-138, 1999.

Kim et al. "Epidermal Growth Factor Receptor Biology", Current Opinion in Oncology, 13(6): 506-513, 2001.

Lappi "Tumor Targeting Through Fibroblast Growth Factor Receptors", Seminars in Cancer Biology, 6: 279-288, 1995.

Nagane et al. "Drug Resistance of Human Glioblastoma Cells Conferred by A Tumor-Specific Mutant Epidermal Growth Factor Receptor Through Modulation of Bcl-XL and Caspase-3-Like Proteases", Proc. Natl. acad. Sci. USA, 95: 5724-5729, 1998.

Nakamura et al. "Effect of Interferon Inducer (Poly ICLC) in the Treatment of Malignant Brain Tumor", No To Shinkei, 34(3): 267-273, 1982. Abstract, Article in Japanese. Abstract in English.

Nishikawa et al. "A Mutant Epidermal Growth Factor Receptor Common in Human Glioma Confers Enhanced Tumorgenicity", Proc. Natl. Acad. Sci. USA, 91: 7727-7731, 1994.

Player et al. "The 2-5A System: Modulation of Viral and Cellular Processes Through Acceleration of RNA Degradation", Pharmacological Therapy, 78(2): 55-113, 1998.

Rosen "Angiogenesis Inhibition in Solid Tumors", Cancer Journal, 7(Suppl.3): 120-128, 2001.

Salazar et al. "Long-Term Treatment of malignant Gliomas With Intramuscularly Administered Polyinosinic-Polycytidylic Acid Stabilized With Polylysine and Carboxymethylcellulose: An Open Pilot Study", Congress of Neurological Surgeons, 38(6): 1096-1104, 1996.

Shir et al. "Gene Therapy for Glioblastoma: Future Perspective for Delivery Systems and Molecular Targets", Cellular and Molecular Neurobiology, 21(6): 645-656, 2001.

Singh "Transferrin as A Targeting Ligand for Liposomes and Anticancer Drugs", Current Pharmaceutical Design, 5: 443-451, 1999.

Von Schwedler et al. "The Nuclear Localization Signal of the Matrix Protein of Human Immunodeficiency Virus Type 1 Allows the Establishment of Infection in Macrophages and Quiescent T Lymphocytes", Proc. Natl. Acad. Sci. USA, 91: 6992-6996, 1994.

Wang et al. "Insulin-Like Growth Factor Receptor-1 as An Anti-Cancer Target: Blocking Transformation and Inducing Apoptosis", Current Cancer Drug Targets, 2: 191-207, 2002.

Communication Pursuant to Article 94(3) EPC Dated Mar. 11, 2009 From the European Patent Office Re.: Application No. 03772616.3.

Communication Pursuant to Article 94(3) EPC Dated Oct. 23, 2009 From the European Patent Office Re.: Application No. 03772616.3.

Supplementary European Search Report Dated Aug. 8, 2006 From the European Patent Office Re.: Application No. 03772616.3.

Translation of Notice of Reason for Rejection Dated Mar. 12, 2010 From the Japanese Patent Office Re.: Application No. 2004-553056.

Chacko et al. "Double-Stranded Ribonucleic Acid Decreases C6 Rat Glioma Cell Proliferation in Part by Activating Protein Kinase R and Decreasing Insulin-Like Growth Factor I Levels", Endocrinology, 143(6): 2144-2154, Jun. 2002.

Collins et al. "Gene and Chromosomal Alterations Associated With the Development of Human Gliomas", The FASEB Journal, 7(10): 926-930, 1993.

International Search Report Dated Jun. 1, 2004 From the International Searching Authority Re.: Application No. PCT/IL03/00957.

Communication Pursuant to Article 96(2) EPC Dated Nov. 17, 2006 From the European Patent Office Re.: Application No. 03772616.3.

Response Dated Apr. 11, 2010 to Communication Pursuant to Article 94(3) EPC of Oct. 23, 2009 From the European Patent Office Re.: Application No. 03772616.3.

* cited by examiner

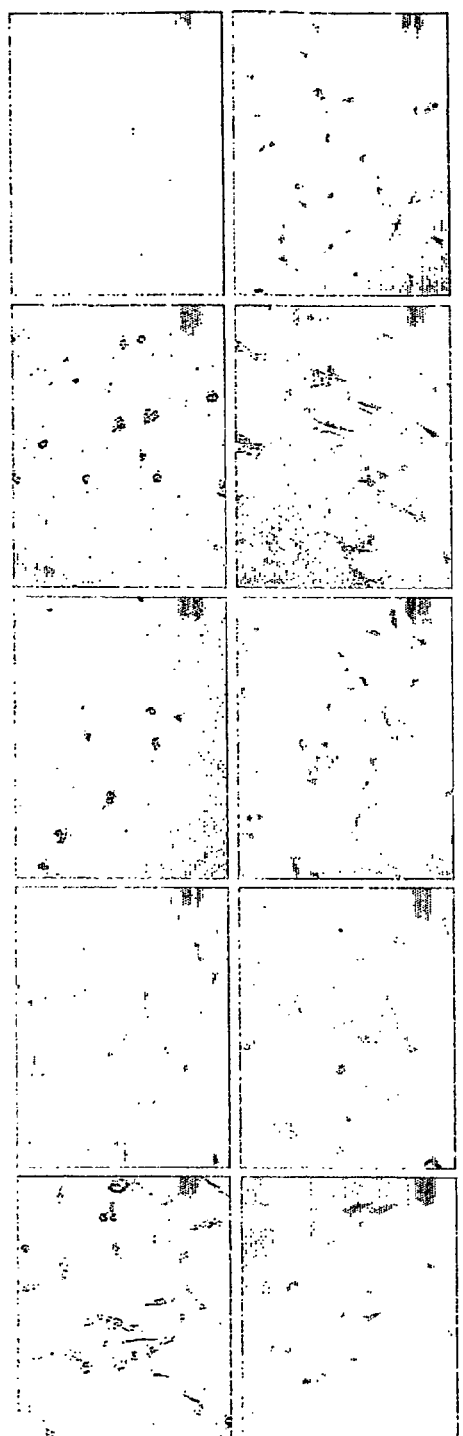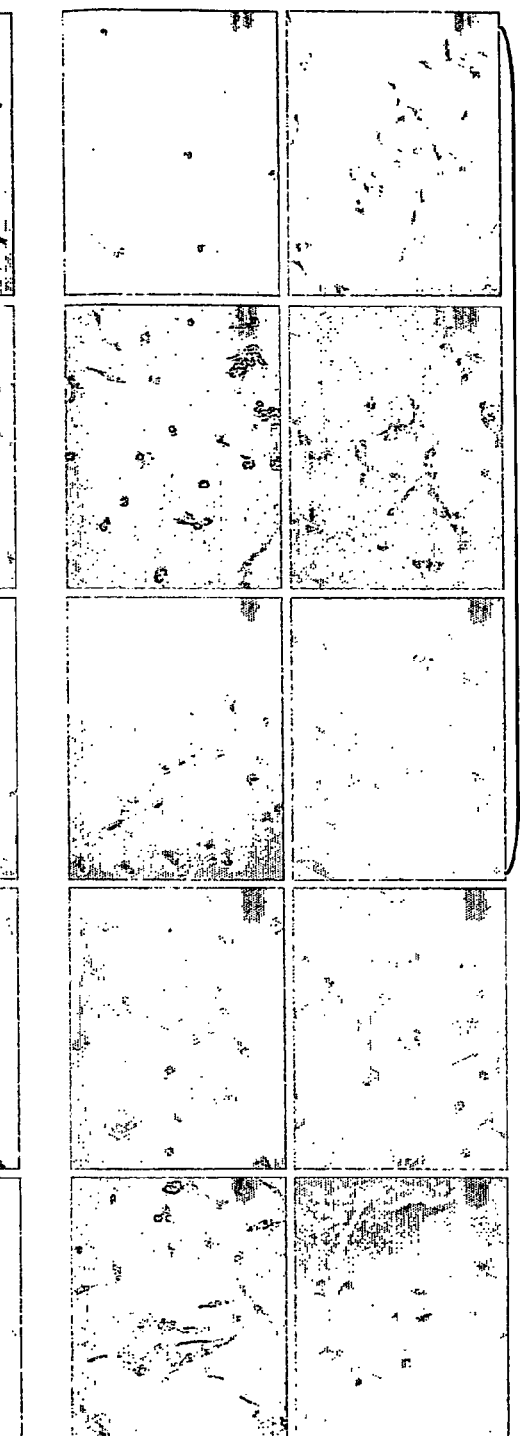

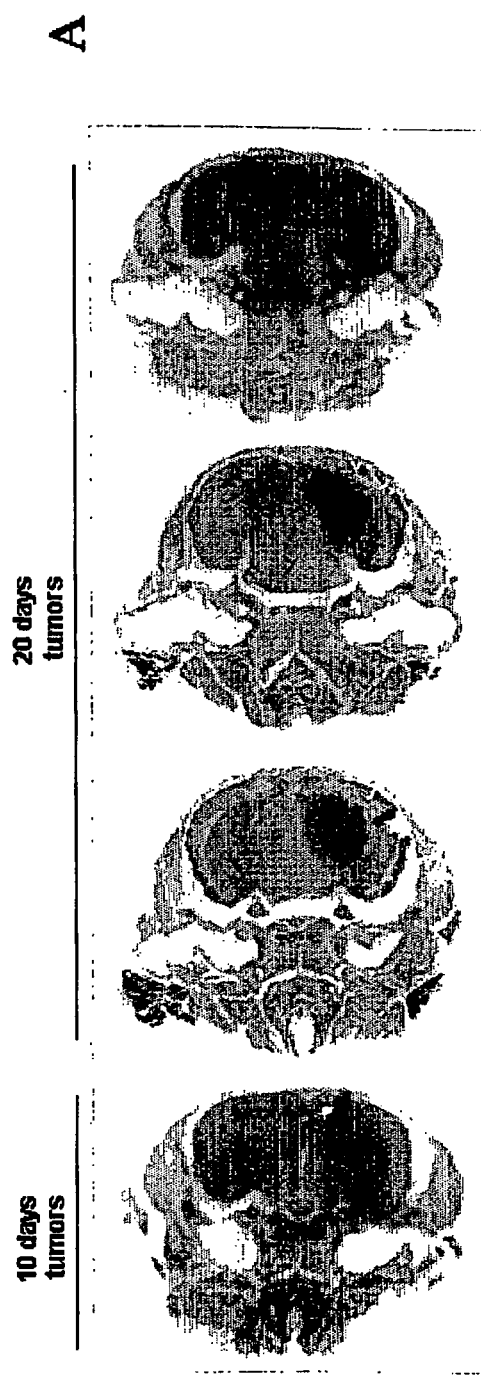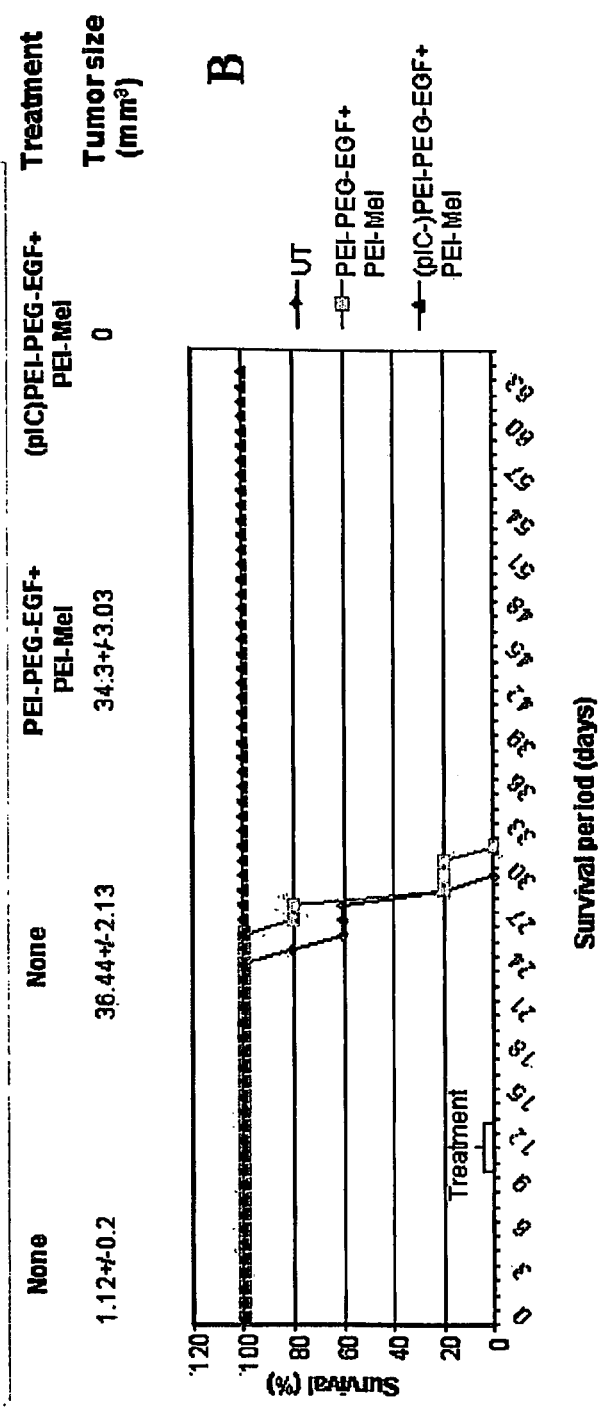
Fig. 11a
Fig. 11b

US 7,927,792 B2

TARGETED DOUBLE STRANDED RNA MEDIATED CELL KILLING

RELATED PATENT APPLICATION

This application is a National Phase Application of PCT/IL03/00957 having International Filing Date of 12 Nov. 2003, which claims the benefit of U.S. Provisional Patent Application No. 60/426,876 filed 18 Nov. 2002.

FIELD AND BACKGROUND OF THE INVENTION

The present invention relates to a composition-of-matter which includes a double stranded RNA (dsRNA) molecule associated with a targeting moiety selected capable of targeting to a specific cell and/or tissue type and to uses of such compositions-of-matter for killing a specific target cell and/or tissue type. Diseases associated with cells/tissue displaying a specific surface marker, such as central nervous system malignancies, include numerous diseases having vast medical and economic impact for which no satisfactory treatment is available.

Malignant gliomas, the most common adult-onset neurological neoplasms, encompass a family of primary central nervous system tumors including glioblastoma, astrocytoma, oligodendroglioma, and ependymoma, along with the juvenile onset neoplasms such as juvenile pilocystic astrocytoma.

Malignant gliomas are typically characterized by overexpression of growth factors/tumor associated antigens believed to significantly contribute to the unchecked growth of such tumors. Various malignant gliomas, such as glioblastomas, exhibit epidermal growth factor receptor (EGFR) overexpression leading to increased aggressiveness and poor prognosis (Kleihues P. and Ohgaki H., 1999. Neuro-oncol. 1999 January; 1(1):44-51; Krishnan et al., 2003. Front Biosci. 8:e1-13). Malignant gliomas may also display overexpression of platelet-derived growth factor receptor (Shapiro W R. and Shapiro J R., 1998. Oncology (Huntingt). February; 12(2):233-40; Feldkamp et al., 1997. J Neurooncol. 1997 December; 35(3):223-48), a phenomenon which has also been correlated with increased malignancy and poor prognosis.

Malignant gliomas, the most common type of primary brain tumors, are aggressive, highly invasive, and neurologically destructive tumors which are among the deadliest of all human cancers. Of the estimated 17,000 new brain tumors diagnosed each year in the United States, about half are malignant gliomas. Malignant glioma cells produce very invasive brain tumors with infiltration of both white and gray matter (Bjerkvig et al., 1986. Cancer Res. 46:4071-912). At the time of diagnosis, microscopic extension through much of the neural axis by malignant glioma is the rule (Burger et al., 1980. Cancer 46:1179-86; Kelly et al., 1987. J. Neurosurg. 66:865-74; Moser, 1988. Cancer 62:381-90; and Salazar et al., 1976. Int. J. Radiat. Oncol. Biol. Phys. 1:627-37). Such extension by motile invading cells underlies the incurability by surgery of most gliomas, even when they appear small and restricted in nature. Glioblastoma multiforme (GBM), the most serious form of malignant glioma, are extremely aggressive brain tumors which generally arise in the upper brain (cerebrum), but which may also occur elsewhere in the central nervous system, such as in the spinal cord, cerebellum, brain stem, or optic chiasm. Low-grade gliomas, which include astrocytomas, oligodendrogliomas, and pilocytic astrocytomas, account for 25% of all primary brain tumors, and over time most of these low-grade tumors dedifferentiate into more malignant gliomas. Diffuse astrocytomas are predominantly located in the cerebral hemispheres of adults and have an inherent tendency to progress to anaplastic astrocytoma and (secondary) glioblastoma. The majority of glioblastomas develop de novo (primary glioblastomas), without an identifiable less-malignant precursor lesion (Kleihues P. and Ohgaki H., 2000. Toxicol Pathol. 2000 January-February; 28(1):164-70). No significant therapeutic advances have been made in treatment of malignant gliomas since the landmark Brain Tumor Cooperative Group studies over 20 years ago demonstrated a survival advantage for patients with malignant gliomas who received radiation and single agent chemotherapy (Walker et al., 1978. J. Neurosurg. 49:333-43; and Walker et al., 1980. NEJM 303:1323-9). While cutting edge molecular technologies have led to a better understanding of glioma biology, these have not yet yielded clinical dividends. Glioblastoma in particular is characterized by resistance to standard treatment modalities including surgery, radiation therapy and chemotherapy. While radiation therapy is the standard treatment after surgical resection, these tumors invariably recur and are associated with a uniformly dismal prognosis, and despite several decades of technological advances in neuro-surgery and radiation therapy there has been no significant change to the overall statistics, with the median survival of patients diagnosed with glioblastoma ranging from 9 to 12 months.

Due to the highly restricted localization of malignant gliomas to the central nervous system and the fact that these tumors do not generally generate remote metastases, various gene therapy approaches have been suggested for their treatment (Bansal, K., and Engelhard, H. H., 2000. Curr Oncol Rep 2, 463-72; Shir, A., and Levitzki, A., 2001. Cell Mol Neurobiol 21, 645-56). While prior art gene therapy approaches involving co-injection of gene expression vectors simultaneously with tumor cells may display a measure of effectiveness when tested in-vitro and in-vivo, such approaches have failed to demonstrate satisfactory effectiveness when tested against established tumors, such as would be the case in the clinical setting. Prior art gene therapy approaches employing viral vectors for treatment of glioblastoma have failed to demonstrate satisfactory infection efficiency. This is thought to be due to the histological structure of glioblastoma which is a highly dense tumor, almost completely impermeable to penetration by particles the size of viruses or larger.

Hence, there is a long-felt and urgent need for novel and optimal methods of selectively killing disease associated cells displaying a specific surface marker, such as glioblastoma cells.

One of the mechanisms which virally infected cells employ to protect the body from infection involves triggering of apoptosis by dsRNA molecules which are generally and exclusively expressed in virally infected cells. Virally induced generation of dsRNA leads to up-regulation of interferon (IFN)-$\alpha/\beta$ expression. Interferon-$\alpha/\beta$ are strong antiproliferative cytokines whose mechanism of action involves inducing expression of PKR and the 2'-5' OAS system for preventing the spread of the virus to cells adjacent to the infected cells. The enzyme PKR is a Ser/Thr protein kinase which upon activation by dsRNA phosphorylates the $\alpha$ subunit of protein synthesis initiation factor eIF-2. This results in sequestration of GDP/GTP exchange factor eIF-2B and rapid inhibition of translation initiation (Farrell et al., 1978. Proc Natl Acad Sci USA 75, 5893-7). Activation of PKR strongly induces cell death by apoptosis which is partly driven by inhibition of the protein synthetic machinery (Jagus, R. et al., 1999. Int J Biochem Cell Biol. 31, 123-38). It is likely that activation of NF-κB, also induced by PKR, prevents immediate cell death allowing production of IFN-α/β. Mechanisms involved in the pro-apoptotic activity of dsRNA also include activation by dsRNA of the 2'-5' Oligo A synthetase/RNase L system which contributes to the shut off of protein synthesis (Player, M. R., and Torrence, P. F., 1998. Pharmacol Ther 78, 55-113), activation of the stress kinases JNK and p38 (Iordanov, M. S. et al., 2000. Mol Cell Biol. 20, 617-27), activation of transcription factors IRF3 and DRAF1 leading to enhanced expression of several proapoptotic genes, and activation of expression of NO synthetase leading to production of NO and subsequent cell death. Hence, dsRNA is a highly potent anti-proliferative/cytoxic molecule capable of killing cells via multiple mechanisms (FIG. 1).

Thus, an optimal strategy for treating diseases, such as malignant glioma, would be to use dsRNA to kill disease associated cells/tissues.

Several prior art approaches have been employed or suggested in order to use dsRNA for selectively killing disease associated cells or tissues, such as malignant glioma cells or tissues.

One approach involves administering polylysine/carboxymethylcellulose stabilized pIC intramuscularly to malignant glioma patients (Salazar, A. M. et al., 1996. Neurosurgery 38, 1096-103).

Another approach involves administering polylysine/carboxymethylcellulose stabilized pIC intravenously to glioblastoma, astrocytoma and ependymoma patients (Nakamura, O. et al., 1982. No To Shinkei 34, 267-73).

Yet another approach involves treating nude mice bearing established intracranial tumors derived from a human glioblastoma cell line by tumor-proximal injection of plasmid vector encoding an anti-sense RNA complementary to RNA transcript of Δ(2-7) EGFR, a mutant form of EGFR specifically expressed in glioblastoma, so as to generate an intracellular dsRNA capable of specifically inducing apoptosis of such cells (Ogris, M. et al., 2001. AAPS PharmSci 3:E21).

All of the aforementioned approaches, however, suffer from significant disadvantages. Namely, approaches employing administration of dsRNA to human patients failed to demonstrate optimal therapeutic results, involve the risk of toxic side-effects such as fever, hypotension and leucopenia, and approaches employing mouse models of human disease failed to demonstrate optimal therapeutic effect, have not demonstrated effectiveness in human patients, and are limited to killing of disease associated cells expressing a highly specific mutant RNA. Moreover, none of these approaches are of optimal safety since none of these have the capacity to selectively target the therapeutic reagent exclusively to the target cells, thereby risking unpredictable and potentially harmful side-effects by interaction with non-targeted cells/tissues.

Thus, all prior art approaches have failed to provide an adequate solution for using dsRNA for killing disease associated cells or tissues.

There is thus a widely recognized need for, and it would be highly advantageous to have, a method of using dsRNA for killing disease associated cells or tissues devoid of the above limitation.

SUMMARY OF THE INVENTION

According to one aspect of the present invention there is provided a method of killing a specific target cell and/or tissue, the method comprising exposing the specific target cell and/or tissue to a composition-of-matter comprising a double stranded RNA molecule associated with a targeting moiety selected capable of targeting to the specific target cell and/or tissue, thereby killing the specific target cell and/or tissue.

According to further features in preferred embodiments of the invention described below, exposing the specific target cell and/or tissue to the composition-of-matter is effected by administering the composition-of-matter to a vertebrate subject bearing the specific target cell and/or tissue.

According to still further features in the described preferred embodiments, administering the composition-of-matter to the vertebrate subject is effected by administering the composition-of-matter to the vertebrate subject systemically and/or to a central nervous system location of the vertebrate subject.

According to another aspect of the present invention there is provided a composition-of-matter comprising a double stranded RNA molecule associated with a targeting moiety selected capable of targeting to a specific cell and/or tissue type.

According to yet another aspect of the present invention there is provided a pharmaceutical composition comprising a pharmaceutically acceptable carrier and as an active ingredient a composition-of-matter which comprises a double stranded RNA molecule associated with a targeting moiety selected capable of targeting to a specific cell and/or tissue type.

According to further features in preferred embodiments of the invention described below, the composition-of-matter further comprises a nucleic acid carrier.

According to still further features in the described preferred embodiments, the targeting moiety is non covalently attached to the double-stranded RNA molecule.

According to still further features in the described preferred embodiments, the targeting moiety is covalently attached to the nucleic acid carrier.

According to still further features in the described preferred embodiments, the double stranded RNA molecule is non covalently attached to the nucleic acid carrier.

According to still further features in the described preferred embodiments, the nucleic acid carrier comprises a polycationic polymer.

According to still further features in the described preferred embodiments, the polycationic polymer is polyethylenimine.

According to still further features in the described preferred embodiments, the nucleic acid carrier comprises a non-ionic water-soluble polymer, a polyether polymer and/or a biocompatible polymer.

According to still further features in the described preferred embodiments, the nucleic acid carrier comprises poly (ethylene glycol).

According to still further features in the described preferred embodiments, the targeting moiety is a ligand of a surface marker of the specific cell and/or tissue type.

According to still further features in the described preferred embodiments, the composition-of-matter further comprises a compound capable of facilitating degradation of an endosomal membrane.

According to still further features in the described preferred embodiments, the compound capable of facilitating degradation of an endosomal membrane is melittin or a melittin derivative.

According to still further features in the described preferred embodiments, the ligand of the surface marker is a biological ligand of the surface marker.

According to still further features in the described preferred embodiments, the targeting moiety is an antibody or antibody fragment.

According to still further features in the described preferred embodiments, the targeting moiety is a growth and/or differentiation factor.

According to still further features in the described preferred embodiments, the growth and/or differentiation factor is epidermal growth factor.

According to still further features in the described preferred embodiments, the surface marker is a growth factor receptor, a differentiation factor receptor and/or a tumor associated antigen.

According to still further features in the described preferred embodiments, the surface marker is epidermal growth factor receptor.

According to still further features in the described preferred embodiments, the double stranded RNA molecule comprises a polyinosinic acid strand and/or a polycytidylic acid strand.

According to still further features in the described preferred embodiments, the double stranded RNA molecule is composed of RNA strands each of which composed of a number of ribonucleotides selected from a range of 10-3,000 ribonucleotides.

According to still further features in the described preferred embodiments, the specific cell and/or tissue type is associated with a disease and/or is a nervous system cell and/or tissue.

According to still further features in the described preferred embodiments, the specific cell and/or tissue type is a tumor cell and/or tissue and/or is a glial cell and/or tissue.

According to still further features in the described preferred embodiments, the specific cell and/or tissue type is a malignant glioma cell and/or tissue.

According to still further features in the described preferred embodiments, the specific cell and/or tissue type is a glioblastoma cell and/or tissue.

According to still further features in the described preferred embodiments, the specific cell and/or tissue type is a human cell and/or tissue.

The present invention successfully addresses the shortcomings of the presently known configurations by providing a method of using dsRNA to kill with optimal selectivity, efficacy, and rapidity an optimally broad range of target cells and/or tissue types in-vitro or in-vivo.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 3a and 3b are a pair of representative fluorescent photomicrographs of sections from the tumor periphery (see FIG. 3f, "P" section) at 1× or 20× original magnification, respectively. FIGS. 3c and 3d are a pair of representative fluorescent photomicrographs of tumor sections from the tumor center/injection site (see FIG. 3f, "C" section) at 1× or 20× original magnification, respectively. FIG. 3e is a fluorescent photomicrograph of a tumor section located at an intermediate distance between the tumor periphery and the tumor center/injection site (see FIG. 3f, "I" section) at 20× original magnification. FIG. 3f is a schematic diagram depicting the cryostat sectioning scheme; P—peripheral section, I—intermediate section, C—center/injection site section. The black triangle indicates the path of lentiviral vector injection and the red lining indicates areas of maximal exposure to lentiviral rector. In the photomicrographs, ADOBE PHOTOSHOP software was used to invert the normal green color of GFP positive cells to red and to contrast-enhance their visibility.

FIGS. 5a-b are photomicrographs depicting high levels of apoptosis in U87MGwtEGFR glioblastoma cells 1 hour following transfection with pIC:PEI$_{25}$-PEG-EGF complex. Prior to transfection, 10,000 cells in a volume of 1 ml medium were seeded per well in 24-well plates and grown overnight. Cells were then transfected with the indicated concentration of pIC using the indicated reagent. One hour after transfection apoptotic death was detected using Annexin or Tunel staining kits (Roche; FIGS. 5a and 5b, respectively). UT—untransfected.

FIGS. 10e and 10f depict the effect on growth of U87MGwtEGFR cells, after 48 and 24 hours, respectively, of culture medium conditioned with U87MGwtEGFR cells transfected with pIC:PEI$_{25}$-PEG-EGF+PEI$_2$-Mel complex at the indicated pIC concentrations, where the conditioned medium has been untreated (24, 48, 72 hours posttransfection) or treated (24L, 48L, 72L hours posttransfection) with the EGFR-containing lysate of U87MGwtEGFR cells. The conditioned medium was harvested at the indicated times posttransfection. Note that there is no significant difference in the cell inhibitory activity of the treated or untreated conditioned medium, indicating that the growth inhibitory effect is not due to residual pIC:carrier complex used for transfection. In order to test the effect of conditioned media, 4,000 U87MGwtEGFR cells were seeded in 96-well plates and grown overnight in 200 microliters culture medium. Lysate samples for treatment of the conditioned medium aliquots were generated by incubating 20,000 U87MGwtEGFR cells in 10 microliters lysis buffer, and lysate treatment consisted in incubating 100 microliters of conditioned medium for 2 hours. FIGS. 10g and 10h show that after 48 and 24 hours, respectively, treatment of pIC:PEI$_{25}$-PEG-EGF+PEI$_2$-Mel complex with the EGFR containing lysate (0.5L, 1L, 10L micrograms/ml pIC) indeed has the capacity to abrogate the cell inhibitory activity thereof in U87MGwtEGFR, U87MG, and U87MGΔEGFR cells, relative to untreated complex (0.5, 1, 10 micrograms/ml pIC). pIC:carrier complex in culture medium was treated with lysate by incubation for two hours with lysate samples generated as described above. In order to test the effect of lysate treated and untreated conditioned media and pIC:carrier complex, 4,000 cells, as indicated, were seeded in 96-well plates and grown overnight in 200 microliters culture medium.

FIGS. 11a-b are a series of photographs and a data plot, respectively, depicting that treatment with pIC-PEI-PEG-EGF+PEI-Mel complexes cure mammals bearing lethal glioblastoma tumors displaying wild-type human EGFR. Aliquots of $10^4$ U87MGwtEGFR cells were stereotactically implanted into the brains of 35 nude mice and 10 days later, 5 animals were sacrificed to evaluate size of the tumors. Ten mice were treated with pIC-PEI$_{25}$-PEG-EGF+PEI$_2$-Mel complex, 10 others were treated with an equivalent dose of the PEI$_{25}$-PEG-EGF+PEI$_2$-Mel carrier only. On day 20 post-inoculation (10 days after treatment initiation), 5 animals from each experimental group were sacrificed, their brains were sectioned for evaluation of tumor size (FIG. 11a) and 5 animals were monitored for survival analysis (FIG. 11b). Established 10 day old tumors are indicated by the white arrow (FIG. 11a, left panel). Note the complete absence of tumor (FIG. 11a), and survival beyond 32 days, for at least as long as 64 days post inoculation, exclusively in the mice treated with the dsRNA:carrier complex

DESCRIPTION OF THE PREFERRED EMBODIMENTS

Figure 1:
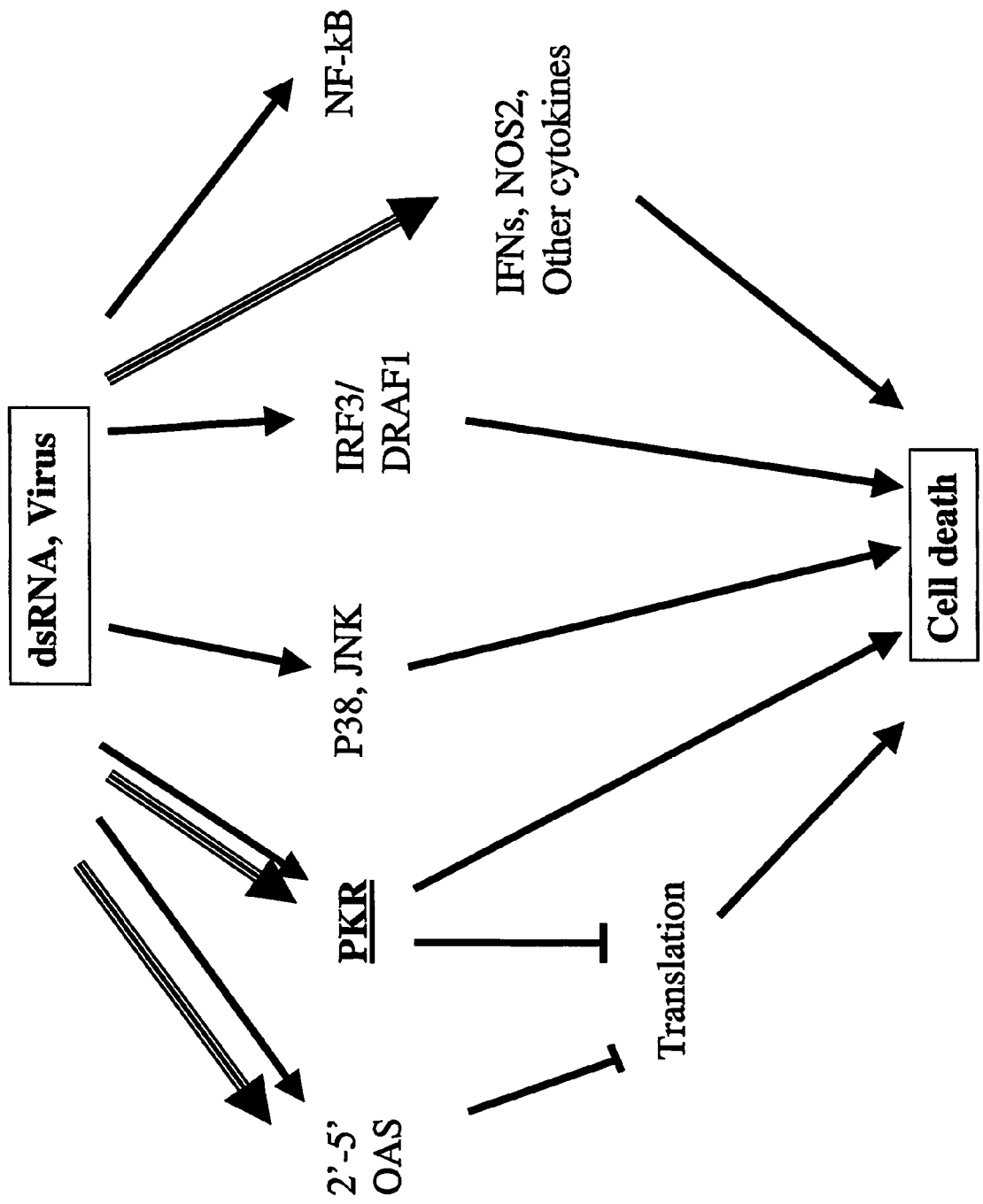
FIG. 1 is a schematic diagram depicting mechanisms of apoptosis induced by double stranded RNA (dsRNA).

The present invention is of a composition-of-matter comprising a double stranded RNA (dsRNA) molecule associated with a targeting moiety selected capable of targeting to a specific cell and/or tissue type, of a pharmaceutical composition comprising as an active ingredient such a composition-of-matter and a pharmaceutically acceptable carrier, and of a method of killing a specific target cell and/or tissue by exposing the specific target cell and/or tissue to such a composition-of-matter. Specifically, the present invention can be used to kill in-vivo with optimal selectivity, rapidity, specificity and safety target cells/tissue displaying a specific surface marker. As such, the method of the present invention is far superior to all prior art methods of killing target cells or tissues displaying a specific surface marker.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Diseases characterized by cells/tissues displaying a specific surface marker, such as glioblastoma overexpressing epidermal growth factor receptor (EGFR), are typically associated with tremendous economic and medical consequences for which no satisfactory treatment is presently available.

Treatment of diseases such as glioblastoma has been attempted using gene therapy approaches based on viral vectors. Such approaches however, are severely hampered by the inability of viral vectors to effectively penetrate and infect tissues such as glioblastoma tissue, by the potential for hazardous genetic recombinations involving replication deficient and especially replication competent viral vectors genetic sequences, and by the potential triggering of lethal/harmful immune/inflammatory responses by viral vectors. Furthermore, such approaches are limited by the critical requirement for gene delivery to the nucleus in target cells, which often requires use of viral vectors with an active nuclear import machinery.

An optimal strategy for treating such diseases involves using dsRNA, an agent having optimal cytotoxic and tissue penetration capacity.

Various approaches for using a dsRNA molecule to selectively kill disease associated cells or tissues, such as malignant glioma cells or tissues, have been described by the prior art.

One approach involves systemically administering a polylysine/carboxymethylcellulose-stabilized polyinosinic acid-polycytidylic acid (pIC) dsRNA molecule to malignant glioma patients, and another approach involves treating nude mice bearing established intracranial tumors derived from a human glioblastoma cell line by tumor proximal injection of plasmid vector encoding an anti-sense RNA complementary to a mutant RNA transcript specifically expressed in such cells so as to generate an intracellular dsRNA molecule capable of specifically inducing apoptosis of such cells.

All of the aforementioned approaches, however, suffer from significant disadvantages, including suboptimal target cell selectivity, failure to demonstrate optimal therapeutic results in humans, risk of toxicity, and/or demonstrated effectiveness restricted to killing of cells specifically expressing a single type of mutant RNA.

Thus, all prior art approaches have failed to provide adequate solutions for using a dsRNA molecule to kill a target cell/tissue with optimal efficacy, safety and/or selectivity.

While reducing the present invention to practice and in attempt to overcome prior art limitations, the present inventors constructed a cytotoxic and yet cell specific dsRNA molecule. This cell-specific cytotoxic dsRNA molecule, was used to kill in-vivo with optimal rapidity, efficiency, and selectivity highly malignant and essentially viral vector-impermeable glioblastoma tumor cells/tissue displaying a specific form of EGFR, thereby traversing many of the limitations of the prior art.

Thus, according to one aspect of the present invention there is provided a method of killing a specific target cell and/or tissue. The method is effected by exposing the target cell/tissue to a composition-of-matter comprising a double stranded ribonucleic acid (RNA) molecule.

By virtue of the optimally high cytotoxicity of the double stranded RNA (dsRNA) molecule of the present invention, as is described and illustrated in the Examples section below, the method can be used for killing the target cell/tissue with optimal efficaciousness and rapidity. Furthermore, as is described hereinbelow and in the Examples section which follows, as a consequence of its optimal tissue penetration capacity, the composition-of-matter of the present invention can be used to kill with optimal efficiency and rapidity a target cell/tissue, such as a human glioblastoma cell/tissue, which is effectively impermeable to particles having the dimensions and/or surface chemistry of a viral vector. Hence, the composition-of-matter of the present invention can be used to kill with optimal efficiency and rapidity a target cell/tissue which is not effectively amenable to killing via a cytotoxic particle such as a viral vector. As such, the method of the present invention overcomes various critical limitations of the prior art.

To enable optimally efficient killing of the target cell/tissue, the method is preferably effected in such a way as to enable optimally efficient delivery of the dsRNA molecule to the target cell/tissue.

The method may be employed to kill the target cell/tissue in any of various contexts, such as in a population of cells cultured in-vitro or, more preferably in-vivo in a vertebrate subject.

Preferably, the vertebrate subject is a mammal, more preferably a human.

The method may be applied to kill essentially any undesired target cell/tissue in a subject in the context of any of various applications.

Preferably, the method is used to kill a target cell/tissue associated with a disease in the subject so as to thereby treat the disease in the subject. It will be appreciated that as a result of enabling optimally efficacious and rapid killing of the target cell/tissue in a subject having a disease associated with the target cell/tissue, the method of the present invention can be used for treating the disease in the subject with optimal effectiveness and rapidity.

When using the method to treat the disease in the subject bearing the target cell/tissue, exposing the target cell/tissue to the composition-of-matter is preferably effected by administering the composition-of-matter to the subject.

The composition-of-matter may be administered to the subject in any of various ways, depending on-the application and purpose.

For example, the composition-of-matter may be advantageously administered to the subject systemically and/or locally.

Preferably, in the case of a disease associated with a target cell/tissue whose location is known and accessible, the composition-of-matter is administered locally to the target cell/tissue. Such localized administration will minimize the possibility of non target cells/tissues being affected by the composition-of-matter, and hence will minimize the possibility of untoward side-effects resulting from such administration. Diseases associated with a target cell/tissue whose location is known and accessible typically include solid tumors. As is described and illustrated in the Examples section below, local administration of the composition-of-matter to a highly malignant human tumor target cell/tissue in a mammalian subject bearing such a target cell/tissue can be used to completely and efficiently cure such a subject of such a tumor.

Preferably, for optimally treating a disease such as a tumor in a human subject, the composition-of-matter is administered intra tumorally.

Alternately, in the case of a disease associated with a target cell/tissue whose location is unknown, diffuse and/or inaccessible, the composition-of-matter may be advantageously administered systemically to facilitate exposure of the composition-of-matter to the target cell/tissue. Due to the optimal biodistribution capacity of the composition-of-matter of the present invention, the composition-of-matter is highly suitable for systemic administration.

Preferably, when administering the composition-of-matter systemically, the composition-of-matter further comprises a targeting moiety of the present invention enabling preferential exposure of the target cell/tissue to the composition-of-matter, as described hereinbelow.

Diseases associated with a target cell/tissue whose location is unknown, diffuse and/or inaccessible include, by way of example, hematological malignancies such as leukemias, metastatic solid tumors; diseases mediated by immune effectors such as autoimmune, allergic and transplantation-related [e.g., graft rejection, graft-versus-host disease (GVHD)] diseases; and neurodegenerative diseases.

Localized and systemic administration may be advantageously combined, for example, to treat a disease, such as a metastatic or potentially metastatic malignancy, whereby, for example, local administration is effected in order to achieve killing of a primary target tumor cell/tissue whose location is known and accessible, and systemic administration is effected in order to achieve optimal killing of a metastatic target cell/tissue whose location is unknown, diffuse and/or inaccessible.

The composition-of-matter may be administered discontinuously or continuously depending on the application and purpose. Preferably, for treating a tumor, the composition-of-matter is administered continuously.

The composition-of-matter may be administered continuously at any of various rates, depending on the application and purpose.

Preferably, when administering the composition-of-matter continuously, the composition-of-matter is administered at a rate corresponding to 1-10 micrograms dsRNA per hour.

The composition-of-matter may be administered for any of various durations, depending on the application and purpose.

Preferably, for treatment of a disease such as a tumor, the composition-of-matter is administered for a duration of 3-14 days.

In large mammals such as humans, intratumoral/peritumoral administration of the composition-of-matter may be achieved using a hydraulic micropump operationally connected to a catheter positioned within or in the vicinity of the tumor, preferably as previously described in Eriksdotter Jonhagen, M. et al., 1998. Dement Geriatr Cogn Disord 9, 246-57.

The composition-of-matter may be administered to the subject per se or as an active ingredient in a pharmaceutical composition including at least one pharmaceutically acceptable carrier. Formulation of the composition-of-matter as an active ingredient in a pharmaceutical composition, and use of such a pharmaceutical composition according to the method of the present invention is described in further detail hereinbelow.

One of ordinary skill in the art, such as a physician, preferably a physician specialized in the disease, will possess the necessary expertise for treating a disease in a human subject according to the teachings of the present invention. Similarly, one of ordinary skill in the art, such as a veterinarian, preferably a veterinarian specialized in the disease, will possess the necessary expertise for treating the disease in an animal according to the teachings of the present invention The method of the present invention envisages the use of any of various types of dsRNA molecules to practice the method of the present invention, depending on the application and purpose.

The dsRNA molecule may be synthetic or derived from any of various natural sources, including cells, bacteria and viruses.

The dsRNA molecule may include non-matching ribonucleotide pairs, but most preferably is wholly composed of matching ribonucleotide pairs.

Matching ribonucleotide pairs includes adenylate (A)-uridylate (U) and inosinate (I) cytidylate (C) pairs.

Each strand of the dsRNA molecule may be composed of any of various mixtures of any of various types of ribonucleotides, including inosinate, cytidylate, adenylate, guanylate and uridylate. Preferably, a strand of the dsRNA molecule is a polymer of a single type or ribonucleotide.

Preferably, the dsRNA molecule includes a polyinosinic acid strand and/or a polycytidylic acid strand. Most preferably, the dsRNA molecule is a polyinosinic acid-polycytidylic acid (pIC) complex. Such a dsRNA molecule may be referred to as poly(I)-poly(C), poly(IC) or poly-IC in the art.

Alternately, the dsRNA molecule may be a polyadenylic acid (pA)-polyuridylic acid (pU) complex. Such a dsRNA molecule may be termed poly(A)-poly(U) in the art.

As described above, the dsRNA molecule may comprise mismatched ribonucleotide pairs. A dsRNA molecule including mismatched ribonucleotide pairs of the present invention is hereinafter referred to as the "mismatched dsRNA molecule."

Preferably, in the mismatched dsRNA molecule hydrogen bonding (base stacking) between counterpart strands is relatively intact, i.e., is interrupted on average less than one base pair in every 29 consecutive base residues. Mismatching results in an interruption of the normal geometry of the dsRNA double helix by in-pouching (or out-pouching) of the strands which represent points of vulnerability of the dsRNA to digestion by ribonucleases.

For example, the mismatched dsRNA molecule may be a polyinosinic acid (pI) strand complexed with polycytidylic acid (pC) strand containing one mismatched uridylate (U) or guanylate (G) ribonucleotide per 5-30 ribonucleotides. Such a mismatched dsRNA molecule is preferably pI-poly($C_4U$), pI-poly($C_7U$), pI-poly($C_{13}U$), pI-poly($C_{22}U$), pI-poly($C_{20}G$), or pI-poly($C_{29}G$). Most preferably, such a mismatched dsRNA molecule is pI-poly($C_{12}U$). A mismatched dsRNA molecule composed of pI complexed with poly$(C_{12}U)_n$, a region consisting of an uninterrupted stretch of 6 to 12 base pairs, i.e., one-half to one full turn of an RNA helix, may serve both as biotrigger causing release of lymphokines and as an obligate intracellular co-factor for enzymes comprising the natural antiviral pathways, and further that such mismatched uridylate ribonucleotides may serve to accelerate dsRNA hydrolysis following cytolysis of target cells/tissues and thus prevent toxicity against non-target cells/tissues (U.S. Pat. No. 5,593,973).

Alternatively, the mismatched dsRNA molecule may include a mismatched ribonucleotide pair in which one of the ribonucleotides has a modified ribosyl backbone, as described, for example in U.S. Pat. Nos. 4,130,641 and 4,024,222. In particular, such a mismatched dsRNA molecule may be a complex of a pC strand and a pI strand having a ribosyl backbone modified, for example, by inclusion of 2'-O-methyl ribosyl residues.

Guidance regarding obtaining and using mismatched dsRNA molecules suitable for practicing the present invention is available in the literature of the art (refer, for example, to: U.S. Pat. No. 5,593,973; European Patent Application EP 0 300 580).

The dsRNA molecule may be composed of a pair of RNA strands composed of a different number, or more preferably, the same number of ribonucleotides.

Each RNA strand of the dsRNA molecule may be composed of any of various numbers of ribonucleotides.

Preferably, each RNA strand of the double stranded RNA molecule is composed of a number of ribonucleotides selected from a range of 10 to 3,000 ribonucleotides, more preferably from a range of 100-300 ribonucleotides.

As is described and illustrated in the Examples section below, a pIC molecule having RNA strands composed of 100-300 ribonucleotides may be employed to kill with optimal rapidity and effectiveness a target cell/tissue of the present invention according to the protocol set forth therein. As is further described therein, exposure of a target cell/tissue to a composition-of-matter of the present invention results in secretion of IFN-α by the target cell tissue, and in growth inhibition of bystander cells. Without being bound to a paradigm, the present inventors are of the opinion that such IFN-α secretion and bystander cell growth inhibition is involved in mediating cytotoxic effect via the dsRNA molecule.

General guidance regarding obtaining and using a dsRNA molecule suitable for practicing the present invention is provided in the literature of the art (refer, for example, to: U.S. Pat. Nos. 4,927,755 and 4,124,702).

Most preferably, the dsRNA molecule is obtained and used as described in the Examples section which follows.

According to the teachings of the present invention, the dsRNA molecule is preferably associated with a targeting moiety selected capable of targeting to the target cell/tissue.

It will be appreciated that association with such a targeting moiety can serve to facilitate optimally efficient delivery of the dsRNA molecule to the target cell/tissue, and thereby to facilitate killing of the target cell/tissue via the dsRNA molecule with optimal selectivity. As such, the targeting moiety will enable killing of the target cell tissue with optimal efficiency while minimizing any possible undesirable side effects resulting from interaction of the dsRNA molecule with non-targeted cells/tissue. Hence, systemic administration of a composition-of-matter which includes such a targeting moiety can be advantageously used to achieve targeted delivery thereof to a specific target cell/tissue whose location is unknown, diffuse and/or inaccessible.

Thus, the present invention provides a composition-of-matter comprising a dsRNA molecule associated with a targeting moiety selected capable of targeting to a specific cell and/or tissue type.

As used herein, the capacity of the targeting moiety of "targeting to a specific cell and/or tissue type", refers to the capacity thereof to selectively home to the proximity of, and/or to selectively associate with, the specific target cell/tissue type.

Without being bound to a paradigm, the present inventors are of the opinion that the capacity of the targeting moiety to selectively home to the proximity of, and/or to selectively associate with, the specific target cell/tissue type serves to facilitate selective homing of the associated dsRNA molecule to the proximity of, and/or selective association of the dsRNA molecule with, the specific target cell/tissue type, and that this, in turn, facilitates specific delivery of the dsRNA molecule to target cell/tissue cytoplasm, and concomitant killing of the target cell/tissue by the dsRNA molecule.

Since, as described hereinbelow, a targeting moiety of the present invention can generally be obtained which is capable of targeting to essentially any surface marker, the composition-of-matter of the present invention can be used for killing essentially any target cell/tissue, and hence for treating in a subject essentially any disease which is associated with such a target cell/tissue and which is amenable to treatment by killing of such a target cell/tissue.

The dsRNA molecule may be associated with the targeting moiety in any of various ways, depending on the application and purpose.

For example, the dsRNA molecule may be covalently associated with, or more preferably non covalently associated with, the targeting moiety.

Non covalent association of the dsRNA molecule with the targeting moiety may be advantageously employed to facilitate disassociation of the dsRNA from the targeting moiety following targeting of the dsRNA molecule to the target cell/tissue, so as to thereby facilitate activation of cell/tissue killing by the free dsRNA molecule. Such non-covalent association will afford the further advantages of being conveniently achieved, and of enabling convenient formation of various dsRNA molecule-targeting moiety complex combinations without the need to resort to cumbersome and/or time-consuming chemical synthesis techniques required for achieving covalent association between molecules.

Alternately, covalent association of the dsRNA molecule with the targeting moiety may be employed to minimize any undesirable tendency of the dsRNA molecule and the targeting moiety to disassociate from each other prior to successful targeting of the dsRNA molecule to the target cell/tissue by the targeting moiety.

According to the teachings of the present invention, non-covalent association of the dsRNA molecule with the targeting moiety is preferably effected via a nucleic acid carrier which is associated with both the dsRNA molecule and the targeting moiety. Suitable nucleic acid carriers for practicing the method of the present invention are described further hereinbelow and in the Examples section which follows.

Preferably, the targeting moiety is covalently attached to the nucleic acid carrier.

Covalent association of molecules such as the nucleic acid carrier, the targeting moiety, and the dsRNA molecule of the present invention may be achieved using any of various chemical and biological methods well known to the ordinarily skilled artisan. For general guidance regarding the practice of such chemical methods, refer, for example, to the extensive guidelines provided by The American Chemical Society (wwwdotchemistrydotorg/portal/chemistry). One of ordinary skill in the art, such as, for example, a chemist, will possess the required expertise for practicing chemical techniques suitable for covalently associating molecules for practicing the present invention.

Preferably, covalent attachment of the targeting moiety to the nucleic acid carrier is achieved as described in the Examples section which follows.

The method of the present invention may be effected using a targeting moiety capable of achieving targeting of the dsRNA molecule to the target cell/tissue via any of various mechanisms, depending on the application and purpose.

Furthermore, the method of the present invention may utilize any of various suitable targeting moieties of the present invention to kill a target cells/tissues displaying any of various surface markers.

As used herein, the phrase "surface marker", refers to any chemical structure which is specifically displayed, displayed at uniquely high density, and/or displayed in a unique configuration by a cell surface or extracellular matrix of the target cell/tissue.

Preferably, the targeting moiety is a specific ligand of the surface marker.

It will be appreciated that such a specific ligand of a surface marker can serve to specifically associate the dsRNA molecule to the target cell/tissue, and to thereby facilitate specific killing of the target cell/tissue via the dsRNA molecule.

Preferably, the targeting moiety is a biological ligand of the surface marker or an antibody or antibody fragment.

Alternately, the targeting moiety may be any molecule, moiety, or chemical structure which can specifically target to the surface marker, such as, for example, a specific surface marker ligand selected from a combinatorial library of affinity ligands.

It will be appreciated that an antibody or antibody fragment specific for essentially any surface marker of the present invention may be routinely generated de novo by one of ordinary skill in the art, or may be obtained by a commercial supplier, as described hereinbelow. A suitable antibody or antibody fragment will in any case be usually available to the ordinarily skilled artisan since an antibody or antibody fragment is generally the sole reagent employed in the art for characterizing display of the surface marker of the present invention on a cell/tissue such as the target cell/tissue of the present invention.

As used herein, the term "antibody" refers to a substantially intact antibody molecule.

As used herein, the phrase "antibody fragment" refers to a functional fragment of an antibody that is capable of binding to a surface marker of the present invention.

Suitable antibody fragments for practicing the present invention include a complementarity-determining region (CDR) of an immunoglobulin light chain (referred to herein as "light chain"), a complementarity-determining region of an immunoglobulin heavy chain (referred to herein as "heavy chain"), a variable region of a light chain, a variable region of a heavy chain, a light chain, a heavy chain, an Fd fragment, and antibody fragments comprising essentially whole variable regions of both light and heavy chains such as an Fv, a single chain Fv, an Fab, an Fab', and an F(ab')$_2$.

Functional antibody fragments comprising whole or essentially whole variable regions of both light and heavy chains are defined as follows:

(i) Fv, defined as a genetically engineered fragment consisting of the variable region of the light chain and the variable region of the heavy chain expressed as two chains;

(ii) single chain Fv ("scFv"), a genetically engineered single chain molecule including the variable region of the light chain and the variable region of the heavy chain, linked by a suitable polypeptide linker.

(iii) Fab, a fragment of an antibody molecule containing a monovalent antigen-binding portion of an antibody molecule which can be obtained by treating whole antibody with the enzyme papain to yield the intact light chain and the Fd fragment of the heavy chain which consists of the variable and $C_H1$ domains thereof;

(iv) Fab', a fragment of an antibody molecule containing a monovalent antigen-binding portion of an antibody molecule which can be obtained by treating whole antibody with the enzyme pepsin, followed by reduction (two Fab' fragments are obtained per antibody molecule); and (v) F(ab')$_2$, a fragment of an antibody molecule containing a monovalent antigen-binding portion of an antibody molecule which can be obtained by treating whole antibody with the enzyme pepsin (i.e., a dimer of Fab' fragments held together by two disulfide bonds).

Methods of generating antibodies (i.e., monoclonal and polyclonal) are well known in the art. Antibodies may be generated via any one of several methods known in the art, which methods can employ induction of in-vivo production of antibody molecules, screening of immunoglobulin libraries (Orlandi D. R. et al., 1989. Proc. Natl. Acad. Sci. U.S.A. 86:3833-3837; Winter G. et al., 1991. Nature 349:293-299) or generation of monoclonal antibody molecules by continuous cell lines in culture. These include, but are not limited to, the hybridoma technique, the human B-cell hybridoma technique, and the Epstein-Barr virus (EBV)-hybridoma technique (Kohler G. et al., 1975. Nature 256:495-497; Kozbor D. et al., 1985. J. Immunol. Methods 81:31-42; Cote R J. et al., 1983. Proc. Natl. Acad. Sci. U.S.A. 80:2026-2030; Cole S P. et al., 1984. Mol. Cell. Biol. 62:109-120).

In cases where target antigens are too small to elicit an adequate immunogenic response when generating antibodies in-vivo, such antigens (haptens) can be coupled to antigenically neutral carriers such as keyhole limpet hemocyanin (KLH) or serum albumin [e.g., bovine serum albumin (BSA)] carriers (see, for example, U.S. Pat. Nos. 5,189,178 and 5,239,078]. Coupling a hapten to a carrier can be effected using methods well known in the art. For example, direct coupling to amino groups can be effected and optionally followed by reduction of the imino linkage formed. Alternatively, the carrier can be coupled using condensing agents such as dicyclohexyl carbodiimide or other carbodiimide dehydrating agents. Linker compounds can also be used to effect the coupling; both homobifunctional and heterobifunctional linkers are available from Pierce Chemical Company, Rockford, Ill. The resulting immunogenic complex can then be injected into suitable mammalian subjects such as mice, rabbits, and the like. Suitable protocols involve repeated injection of the immunogen in the presence of adjuvants according to a schedule which boosts production of antibodies in the serum. The titers of the immune serum can readily be measured using immunoassay procedures which are well known in the art.

The antisera obtained can be used directly or monoclonal antibodies may be obtained as described hereinabove.

Antibody fragments can be obtained using methods well known in the art [(see, for example, Harlow and Lane, "Antibodies: A Laboratory Manual", Cold Spring Harbor Laboratory, New York, (1988)]. For example, antibody fragments according to the present invention can be prepared by proteolytic hydrolysis of the antibody or by expression in *E. coli* or mammalian cells (e.g., Chinese hamster ovary cell culture or other protein expression systems) of DNA encoding the fragment.

Alternatively, antibody fragments can be obtained by pepsin or papain digestion of whole antibodies by conventional methods. As described hereinabove, an (Fab')$_2$ antibody fragments can be produced by enzymatic cleavage of antibodies with pepsin to provide a 5S fragment. This fragment can be further cleaved using a thiol reducing agent, and optionally a blocking group for the sulfhydryl groups resulting from cleavage of disulfide linkages to produce 3.5S Fab' monovalent fragments. Alternatively, enzymatic cleavage using pepsin produces two monovalent Fab' fragments and an Fc fragment directly. Ample guidance for practicing such methods is provided in the literature of the art (for example, refer to: Goldenberg, U.S. Pat. Nos. 4,036,945 and 4,331,647; Porter, R R., 1959. Biochem. J. 73:119-126). Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

As described hereinabove, an Fv is composed of paired heavy chain variable and light chain variable domains. This association may be noncovalent (see, for example, Inbar et al., 1972. Proc. Natl. Acad. Sci. USA. 69:2659-62). Alternatively, as described hereinabove the variable domains can be linked to generate a single chain Fv by an intermolecular disulfide bond, or alternately, such chains may be cross-linked by chemicals such as glutaraldehyde.

Preferably, the Fv is a single chain Fv.

Single chain Fv's are prepared by constructing a structural gene comprising DNA sequences encoding the heavy chain variable and light chain variable domains connected by an oligonucleotide encoding a peptide linker. The structural gene is inserted into an expression vector, which is subsequently introduced into a host cell such as E. coli. The recombinant host cells synthesize a single polypeptide chain with a linker peptide bridging the two variable domains. Ample guidance for producing single chain Fv's is provided in the literature of the art (for example, refer to: Whitlow and Filpula, 1991. Methods 2:97-105; Bird et al., 1988. Science 242:423-426; Pack et al., 1993. Bio/Technology 11:1271-77; and Ladner et al., U.S. Pat. No. 4,946,778).

Isolated complementarity determining region peptides can be obtained by constructing genes encoding the complementarity determining region of an antibody of interest. Such genes may be prepared, for example, by RT-PCR of mRNA of an antibody-producing cell. Ample guidance for practicing such methods is provided in the literature of the art (for example, refer to Larrick and Fry, 1991. Methods 2:106-10).

It will be appreciated that for human therapy or diagnostics, humanized antibodies are preferably used. Humanized forms of non human (e.g., murine) antibodies are genetically engineered chimeric antibodies or antibody fragments having-preferably minimal-portions derived from non human antibodies. Humanized antibodies include antibodies in which complementary determining regions of a human antibody (recipient antibody) are replaced by residues from a complementarity determining region of a non human species (donor antibody) such as mouse, rat or rabbit having the desired functionality. In some instances, Fv framework residues of the human antibody are replaced by corresponding non human residues. Humanized antibodies may also comprise residues which are found neither in the recipient antibody nor in the imported complementarity determining region or framework sequences. In general, the humanized antibody will comprise substantially all of at least one, and typically two, variable domains, in which all or substantially all of the complementarity determining regions correspond to those of a non human antibody and all, or substantially all, of the framework regions correspond to those of a relevant human consensus sequence. Humanized antibodies optimally also include at least a portion of an antibody constant region, such as an Fc region, typically derived from a human antibody (see, for example, Jones et al., 1986. Nature 321:522-525; Riechmann et al., 1988. Nature 332:323-329; and Presta, 1992. Curr. Op. Struct. Biol. 2:593-596).

Methods for humanizing non human antibodies are well known in the art. Generally, a humanized antibody has one or more amino acid residues introduced into it from a source which is non human. These non human amino acid residues are often referred to as imported residues which are typically taken from an imported variable domain. Humanization can be essentially performed as described (see, for example: Jones et al., 1986. Nature 321:522-525; Riechmann et al., 1988. Nature 332:323-327; Verhoeyen et al., 1988. Science 239:1534-1536; U.S. Pat. No. 4,816,567) by substituting human complementarity determining regions with corresponding rodent complementarity determining regions. Accordingly, such humanized antibodies are chimeric antibodies, wherein substantially less than an intact human variable domain has been substituted by the corresponding sequence from a non human species. In practice, humanized antibodies may be typically human antibodies in which some complementarity determining region residues and possibly some framework residues are substituted by residues from analogous sites in rodent antibodies.

Human antibodies can also be produced using various techniques known in the art, including phage display libraries [see, for example, Hoogenboom and Winter, 1991. J. Mol.

Biol. 227:381; Marks et al., 1991. J. Mol. Biol. 222:581; Cole et al., "Monoclonal Antibodies and Cancer Therapy", Alan R. Liss, pp. 77 (1985); Boerner et al., 1991. J. Immunol. 147: 86-95). Humanized antibodies can also be made by introducing sequences encoding human immunoglobulin loci into transgenic animals, e.g., into mice in which the endogenous immunoglobulin genes have been partially or completely inactivated. Upon antigenic challenge, human antibody production is observed in such animals which closely resembles that seen in humans in all respects, including gene rearrangement, chain assembly, and antibody repertoire. Ample guidance for practicing such an approach is provided in the literature of the art (for example, refer to; U.S. Pat. Nos. 5,545,807, 5,545,806, 5,569,825, 5,625,126, 5,633,425, and 5,661,016; Marks et al., 1992. Bio/Technology 10:779-783; Lonberg et al., 1994. Nature 368:856-859; Morrison, 1994. Nature 368: 812-13; Fishwild et al., 1996. Nature Biotechnology 14:845-51; Neuberger, 1996. Nature Biotechnology 14:826; Lonberg and Huszar, 1995. Intern. Rev. Immunol. 13:65-93).

Once antibodies are obtained, they may be tested for activity, for example via ELISA.

As described hereinabove, since a targeting moiety capable of targeting to essentially any desired surface marker can be obtained by the ordinarily skilled artisan, the method of the present invention may be employed to kill a target cell/tissue specifically displaying essentially any such surface marker, and, as such, can be used for treating essentially any disease associated with a cell/tissue displaying such a surface marker.

Ample guidance regarding surface markers specifically overexpressed in diseases such as cancer, and antibodies specific for such surface markers is provided in the literature of the art (for example, refer to: A M Scott, C Renner. "Tumour Antigens Recognised by Antibodies." In: Encyclopedia of Life Sciences, Nature Publishing Group, Macmillan, London, UK, wwwdotelsdotnet, 2001).

Preferably, the method is used to treat a disease associated with a target cell/tissue specifically displaying a surface marker which is a growth factor receptor and/or a tumor associated antigen (TAA).

Diseases associated with a target cell/tissue specifically displaying a growth factor receptor/TAA surface marker which are amenable to treatment by the method of the present invention include, for example, some of the numerous diseases which specifically display growth factor receptors/TAAs, such as EGF receptor, platelet derived growth factor (PDGF) receptor, insulin like growth factor receptor, vascular endothelial growth factor (VEGF) receptor, fibroblast growth factor (FGF) receptor, transferrin receptor, and folic acid receptor. Specific examples of such diseases and the growth factor receptors/TAAs which these specifically display are listed in Table 1, below.

TABLE 1

Examples of malignancies specifically overexpressing growth factor receptors

| Receptor* | Malignancy type | Review reference |
|---|---|---|
| EGF receptor | Malignant glioma, glioblastoma, head and neck, breast, colon, lung, prostate, kidney, ovary, brain, pancreas, bladder | Kim, E. S. et al., 2001. Curr Opin Oncol 13, 506-13; Kuan et al., 2000. Brain Tumor Pathol. 2000; 17: 71-8 |
| PDGF receptor | Brain, prostate | George, D., 2001. Semin Oncol 28, 27-33 |
| IGF receptor | Breast, lung, colon, prostate | Wang, Y., and Sun, Y., 2002. Curr Cancer Drug Targets 2, 191-207 |

TABLE 1-continued

Examples of malignancies specifically overexpressing growth factor receptors

| Receptor* | Malignancy type | Review reference |
|---|---|---|
| VEGF receptor | Solid tumors, acute and chronic leukemias, myeloproliferative diseases, multiple myeloma, non-Hodgkin's lymphomas, and Hodgkin's disease | Rosen, L. S., 2001. Cancer J 7 Suppl 3, S120-8; Giles, F. J., 2001. Oncologist 6, 32-9 |
| FGF receptor | Melanoma, Caposi sarcoma, pancreas | Lappi, D. A., 1995. Semin Cancer Biol 6, 279-88 |
| Transferrin receptor | Leukemia, brain, colon, kidney, bladder | Singh, M., 1999. Curr Pharm Des 5, 443-51 |

*Abbreviations:
EGF—epidermal growth factor,
PDGF—platelet derived growth factor,
IGF—insulin like growth factor,
VEGF—vascular endothelial growth factor,
FGF—fibroblast growth factor.

Preferably, method of the present invention is used for treating a disease associated with a target cell/tissue specifically displaying an EGF receptor (EGFR).

The method may be employed for treating a disease associated with a target cell/tissue specifically displaying a mutant, or more preferably wild type EGFR.

Specific variants/mutants of EGFR are often specifically displayed in cells/tissue of various malignancies. For example, Δ(2-7) EGFR [also referred to as EGFR type III (EGFRvIII) in the art], the most common variant/mutant form of EGFR, has a deletion in its extracellular domain that results in the formation of a new, tumor-specific target found in glioblastoma, as well as in breast, ovarian, prostate, and lung carcinomas. Antibodies specific for this EGFR variant which are suitable for generating a targeting moiety for treating such diseases according to the method of the present invention are available or can be generated de novo (Kuan et al., 2000. Brain Tumor Pathol. 2000; 17:71-8).

Examples of human antibodies approved by the U.S. FDA which are suitable as targeting moiety for treating a malignant disease according to the teachings of the present invention are described in Table 2, below.

TABLE 2

Examples of FDA approved anti-TAA human antibodies.

| Antibody name | Specificity (target antigen) | Company | Disease indication |
|---|---|---|---|
| ABX-EGF* | EGF | Abgenix (Fremont, CA) | colorectal, lung, prostate, renal cancers |
| ABX-IL8*¶ | IL-8 | Abgenix (Fremont, CA) | Melanoma |
| Humaspect Votumumab§ | cytokeratin tumor-associated antigen | Organon Teknika | colon/rectal carcinoma |
| HuMax-EGFR | EGFR | Genmab A/S (Copenhagen, DK) | Cancer |
| HuMax-Lymphoma | | Genmab A/S (Copenhagen, DK)/Immunex Corporation | Lymphoma |

*Mike's Immunoglobulin Structure/Function: Antibodies for Therapeutic Applications
¶PhRMA: New Medicines in Development: Biotechnology: A 2000 Survey
§Biopharmaceutical Benchmarks, Nature Biotechnology, 18, 831-833 (2000)

Preferably, for treating a disease associated with a target cell/tissue specifically displaying wild type EGFR, the targeting moiety is EGF, the biological ligand of EGFR.

The method of the present invention may be used to kill a target cell/tissue which is derived from essentially any type of differentiation lineage.

Preferably, the method of the present invention is used to kill a nervous system derived target cell/tissue type, more preferably a glial cell/tissue, more preferably a malignant glioma cell/tissue, and most preferably a glioblastoma cell/tissue.

Preferably, the specific cell and/or tissue type is a human cell and/or tissue.

As is described and illustrated in the Examples section which follows, a composition-of-matter of the present invention comprising a dsRNA molecule associated with EGF can be used according to the protocol set forth therein to achieve optimally efficacious, rapid and selective killing of a human glioblastoma target cell/tissue specifically displaying EGFR in a mammalian subject bearing such tissue.

Hence, the method of the present invention is optimal for treating in a human subject a malignancy, such as glioblastoma, associated with cells/tissue specifically expressing a growth factor receptor/TAA, such as wild type EGFR.

As described hereinabove, the method may be used to treat essentially any disease associated with a target cell/tissue displaying a specific surface marker. Such diseases further include, by way of example, autoimmune, transplantation related (graft rejection, graft-versus-host disease), and allergic diseases, in which immune effector cells mediating pathogenesis thereof display specific antigen receptors (T-cell receptors, B cell receptors, mast cell displayed FcεR:IgE complex) which may be targeted so as to treat such diseases according to the method of the present invention.

Various methods known to the ordinarily skilled artisan may be employed for testing the cytotoxic activity of the present invention. For example, such cytotoxic activity may be tested in-vitro via any of various assays used for assaying apoptosis. Preferably, such determination of dsRNA induced apoptosis is effected as described in the Examples section below Alternately, an assay for testing activation of PKR in response to treatment with the composition may be employed. Various assays described in the art may be employed for testing activation of PKR (for example, refer to Shir, A., and Levitzki, A., 2001. Cell Mol. Neurobiol 21, 645-56).

Preferably, the composition-of-matter of the present invention further comprises a nucleic acid carrier serving to facilitate optimal killing of the target cell/tissue by the dsRNA molecule.

In order to facilitate optimal killing of the target cell/tissue by the dsRNA molecule, the nucleic acid carrier is selected capable of preventing chemical interaction of the dsRNA molecule with a non cytoplasmic environment, and/or of facilitating delivery of the dsRNA molecule to cytoplasm of the target cell/tissue, most preferably both. Since the cytotoxic effect of dsRNA is mediated intracytoplasmically, a nucleic acid carrier which facilitates delivery of the dsRNA to target cell/tissue cytoplasm will facilitate optimal killing of the target cell/tissue. Furthermore, a nucleic acid carrier which prevents chemical interaction of the dsRNA molecule with a non cytoplasmic environment, such as serum in particular, can serve to prevent, in-vivo and in-vitro, degradation of the dsRNA molecule by the non cytoplasmic environment, and to prevent non specific adhesion of the dsRNA molecule to a non target cell/tissue. Additionally, when administering the composition-of-matter to a subject, such a nucleic acid carrier will minimize the possibility of undesired side effects triggered by the dsRNA molecule in the subject such as immune/inflammatory responses directed against the dsRNA molecule.

Various nucleic acid carriers may be employed, depending on the application and purpose, according the teachings of the present invention.

Preferably, the nucleic acid carrier comprises a polycationic polymer, a non-ionic water-soluble polymer, a polyether polymer and/or a biocompatible polymer, most preferably all of which.

According to standard art knowledge, a polycationic polymer, by virtue of its distributed positive electrostatic charges presents various advantageous characteristics for practicing method of the present invention. For example, a polycationic polymer has the capacity to optimally associate non-covalently with the dsRNA molecule which is a polyanionic polymer having distributed negative electrostatic charges, thereby facilitating neutralization of the negative electrostatic charges of the dsRNA molecule, and hence neutralizing any tendency of the dsRNA to chemically interact with a non cytoplasmic environment. Furthermore, a polycationic polymer having sufficient positive charge will facilitate formation of a positively charged dsRNA:polycationic polymer complex which will tend to adhere to the cell membrane, and undergo endosomal uptake and subsequent cytoplasmic delivery of the dsRNA upon endosomal membrane degradation. Furthermore, the polycationic polymer, as a result of its non covalent association with the dsRNA will be capable of physically separating from the dsRNA under cytoplasmic conditions, thereby allowing the dsRNA to optimally activate cell killing.

The method of the present invention may be practiced using a nucleic acid carrier comprising any of various polycationic polymers suitable for delivery of nucleic acids, such as the dsRNA molecule of the present invention, to cells, depending on the application and purpose.

Preferably, the polycationic polymer is polyethylenimine (PEI).

Alternately, the polycationic polymer may be, for example, poly-L-lysine.

The polyethylenimine of the present invention may be characterized by of any of various combinations of chemical composition and/or molecular weight, depending on the application and purpose, as described hereinbelow and in the Examples section which follows.

Ample guidance for using polycationic polymers for facilitating transfection of nucleic acids, such as the dsRNA molecule of the present invention, into target cells/tissues, such as those of the present invention, is provided in the literature of the art (for example, refer to: Kichler et al., 2001. J Gene Med. 3:135-44; Lecocq et al., 2000. Biochem Biophys Res Commun. 278:414-8; Marschall et al., 1999. Gene Ther. 6:1634-7).

As described hereinabove, the nucleic acid carrier preferably also comprises a non-ionic water-soluble polymer, a polyether polymer and/or a biocompatible polymer, preferably all of which.

The nucleic acid carrier may advantageously comprise any of various non-ionic, water-soluble polymers, polyether polymers and/or biocompatible polymers.

Preferably, the nucleic acid carrier comprises poly(ethylene glycol) (also referred to in the art as PEG or polyethylene glycol), a biocompatible non-ionic/water-soluble, polyether polymer.

Poly(ethylene glycol) is one of the most widely used biologically inert polymers for carrying drugs in-vivo. PEG has a wide range of uses in biomedical applications including PEG-protein conjugates for pharmaceutical applications, and PEG hydrogels for cell encapsulation, drug delivery, and cell purification. PEG has excellent solubility in aqueous and in most organic solutions. Biologically, PEG has favorable pharmacokinetics and tissue distribution, as well as a lack of toxicity and immunogenicity. One of the most desirable features of PEG is its approval by the U.S. Food and Drug Administration (FDA) for in-vivo administration. Ample guidance for selecting and utilizing PEG for practicing the method of the present invention is available in the literature of the art [for general guidance, refer, for example, to Zalipsky, S., Harris, J. M. 1997. Introduction to Chemistry and Biological Applications of Poly(ethylene glycol). Poly(ethylene glycol) Chemistry and Biological Applications. American Chemical Society, San Francisco, Calif. (p. 1-11); for guidance for covalently attaching PEG to molecules, such as therapeutic nucleic acids and polypeptides, refer, for example, to: Molineux G., 2002. Cancer Treat Rev. 28 Suppl A:13-6; Harris J M. and Chess R B., 2003. Nat Rev Drug Discov. 2:214-21; Sato H., 2002. Adv Drug Deliv Rev. 54:487-504; Roberts et al., 2002. Adv Drug Deliv Rev. 54:459-76). Covalent attachment of molecules to PEG may be referred to as "pegylation" in the art.

The PEG of the present invention may be characterized by of any of various combinations of chemical composition and/or molecular weight, depending on the application and purpose, as described hereinbelow and in the Examples section which follows.

Preferably, the PEG of the present invention has a molecular weight selected from the range of 0.34-34 kDa, most preferably of 3.4 kDa.

Preferably, the PEG of the present invention is covalently associated with a polyethylenimine of the present invention.

Preferably, when conjugating a polyethylenimine of the present invention to a PEG of the present invention, the polyethylenimine is branched and has a molecular weight of 2.5-250 kDa, most preferably of about 25 kDa. Preferably, a 25 kDa PEI of the present invention has a molecular weight of 25 kDa as determined by light scattering. Covalent association of the polyethylenimine with the PEG of the present invention is preferably effected as described in the Examples section below.

As used herein the term "about" refers to plus or minus 10%.

As is described in the Examples section below, a composition-of-matter comprising PEG covalently associated with polyethylenimine (2 kDa) can be used for effectively practicing the method of the present invention.

In order to facilitate optimal killing of the target cell/tissue by the dsRNA molecule, the composition-of-matter of the present invention preferably further comprises a compound capable of facilitating degradation of an endosomal membrane.

It will be appreciated that, since a composition-of-matter of the present invention will generally be endocytosed into target cell/tissue endosomes, such a compound capable of facilitating degradation of an endosomal membrane will facilitate release of the dsRNA molecule from a target cell/tissue endosome into cytoplasm thereof. As a consequence, this will enhance killing of the target cell/tissue by the dsRNA molecule which requires cytoplasmic localization in order to optimally mediate cytotoxicity.

Any of various compounds capable of facilitating degradation of an endosomal membrane (hereinafter referred to as "membrane antagonist") may be employed.

Preferably, the membrane antagonist is melittin or a melittin derivative.

Melittin is a cationic peptide which is a membrane lytic component of bee sting venom (Dempsey, C. E., 1990. Biochim. Biophys. Acta 1031, 143-161). Ample guidance for using melittin to facilitate transfection of nucleic acids, such as the dsRNA molecule of the present invention, into target cells/tissues, such as those of the present invention, is provided in the literature of the art (for example, refer to Ogris et al., 2001. J. Biol. Chem. 276, 47550-47555).

Preferably, the melittin or melittin derivative is a peptide which includes the amino acid sequence set forth in SEQ ID NO: 1. A peptide having the amino acid sequence set forth in SEQ ID NO: 1 is generally referred to as melittin in the art.

As used herein, the term "peptide" refers to a polypeptide of less than 51 amino acid residues or modified amino acid residues.

Alternately, the membrane antagonist may be a peptide comprising any of various amino acid sequences capable of facilitating degradation of an endosomal membrane.

Guidance for obtaining and utilizing a peptide according to the present invention is provided hereinbelow.

The membrane antagonist may be incorporated into the composition-of-matter in any of various ways.

Preferably, the membrane antagonist is covalently associated with a polycationic polymer of the present invention, more preferably a polyethylenimine of the present invention, more particularly a polyethylenimine having a molecular weight selected from a range of 0.2 to 20 kDa, and most preferably a polyethylenimine having a molecular weight of about 2 kDa.

The membrane antagonist may be covalently associated with a polycationic polymer of the present invention in any of various ways.

Preferably, the membrane antagonist is covalently associated with a polycationic polymer of the present invention according to the protocol described in the Examples section below.

As is described and illustrated in the Examples section which follows, incorporation of a polypeptide having the amino acid sequence set forth in SEQ ID NO: 1 covalently associated with a polyethylenimine (2 kDa) in a composition-of-matter of the present invention will significantly enhance the capacity of the composition-of-matter to kill a target cell/tissue of in various in-vitro and in-vivo contexts.

As described hereinabove, the membrane antagonist may be peptide comprising any of various amino acid sequences.

As used herein, the term "peptide" includes native peptides (either degradation products, synthetically synthesized peptides or recombinant peptides) and peptidomimetics (typically, synthetically synthesized peptides), such as peptoids and semipeptoids which are peptide analogs, which may have, for example, modifications rendering the peptides more stable while in a body, in-vitro or more capable of penetrating into target cell/tissue cytoplasm. Such modifications include, but are not limited to N terminus modification, C terminus modification, peptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992).

Peptide bonds (—CO—NH—) within the peptide may be substituted, for example, by N-methylated bonds (—N(CH3)-CO—), ester bonds (—C(R)H—C—O—O—C(R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH=CH—), retro amide bonds (—NH—CO—), peptide derivatives (—N(R)—CH2-CO—), wherein R is the "normal" side chain, naturally presented on the carbon atom.

These modifications can occur at any of the bonds along the peptide chain and even at several (2-3) at the same time.

Natural aromatic amino acids, Trp, Tyr and Phe, may be substituted for synthetic non-natural acid such as TIC, naphthylelanine (Nol), ring-methylated derivatives of Phe, halogenated derivatives of Phe or o-methyl-Tyr.

In addition to the above, the peptides of the present invention may also include one or more modified amino acids or one or more non-amino acid monomers (e.g. fatty acids, complex carbohydrates etc).

As used herein in the specification and in the claims section below the term "amino acid" or "amino acids" is understood to include the 20 naturally occurring amino acids; those amino acids often modified post-translationally in-vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Tables 3 and 4 below list naturally occurring amino acids, and non-conventional or modified amino acids, respectively, which can be used with the present invention.

The peptides of the present invention can be utilized in a linear or cyclic form.

A peptide can be either synthesized in a cyclic form, or configured so as to assume a cyclic structure under suitable conditions.

For example, a peptide according to the teachings of the present invention can include at least two cysteine residues flanking the core peptide sequence. In this case, cyclization can be generated via formation of S—S bonds between the two Cys residues. Side-chain to side chain cyclization can also be generated via formation of an interaction bond of the formula —(—CH2-)n-S—CH-2-C—, wherein n=1 or 2, which is possible, for example, through incorporation of Cys or homoCys and reaction of its free SH group with, e.g., bromoacetylated Lys, Orn, Dab or Dap. Furthermore, cyclization can be obtained, for example, through amide bond formation, e.g., by incorporating Glu, Asp, Lys, Orn, di-amino butyric (Dab) acid, di-aminopropionic (Dap) acid at various positions in the chain (—CO—NH or —NH—CO bonds). Backbone to backbone cyclization can also be obtained through incorporation of modified amino acids of the formulas H—N((CH2)n-COOH)—C(R)H—COOH or H—N((CH2)n-COOH)—C(R)H—NH2, wherein n=1-4, and further wherein R is any natural or non-natural side chain of an amino acid.

TABLE 3

Naturally occurring amino acids.

| Amino Acid | Three-Letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |

TABLE 3-continued

Naturally occurring amino acids.

| Amino Acid | Three-Letter Abbreviation | One-letter Symbol |
|---|---|---|
| Glycine | Gly | G |
| Histidine | His | H |
| Isoleucine | Iie | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid as above | Xaa | X |

TABLE 4

Non-conventional or modified amino acids.

| Non-conventional amino acid | Code |
|---|---|
| α-aminobutyric acid | Abu |
| α-amino-α-methylbutyrate | Mgabu |
| aminocyclopropane-carboxylate | Cpro |
| aminoisobutyric acid | Aib |
| aminonorbornyl-carboxylate | Norb |
| cyclohexylalanine | Chexa |
| cyclopentylalanine | Cpen |
| D-alanine | Dal |
| D-arginine | Darg |
| D-aspartic acid | Dasp |
| D-cysteine | Dcys |
| D-glutamine | Dgln |
| D-glutamic acid | Dglu |
| D-histidine | Dhis |
| D-isoleucine | Dile |
| D-leucine | Dleu |
| D-lysine | Dlys |
| D-methionine | Dmet |
| D-ornithine | Dorn |
| D-phenylalanine | Dphe |
| D-proline | Dpro |
| D-serine | Dser |
| D-threonine | Dthr |
| D-tryptophan | Dtrp |
| D-tyrosine | Dtyr |
| D-valine | Dval |
| D-α-methylalanine | Dmala |
| D-α-methylarginine | Dmarg |
| D-α-methylasparagine | Dmasn |
| D-α-methylaspartate | Dmasp |
| D-α-methylcysteine | Dmcys |
| D-α-methylglutamine | Dmgln |
| D-α-methylhistidine | Dmhis |
| D-α-methylisoleucine | Dmile |
| D-α-methylleucine | Dmleu |
| D-α-methyllysine | Dmlys |
| D-α-methylmethionine | Dmmet |
| D-α-methylornithine | Dmorn |
| D-α-methylphenylalanine | Dmphe |
| D-α-methylproline | Dmpro |
| D-α-methylserine | Dmser |
| D-α-methylthreonine | Dmthr |
| D-α-methyltryptophan | Dmtrp |
| D-α-methyltyrosine | Dmty |
| D-α-methylvaline | Dmval |
| D-N-methylalnine | Dnmala |
| D-α-methylarginine | Dnmarg |
| D-α-methylasparagine | Dnmasn |
| D-α-methylasparatate | Dnmasp |
| D-α-methylcysteine | Dnmcys |
| D-N-methylleucine | Dnmleu |

TABLE 4-continued

Non-conventional or modified amino acids.

| Non-conventional amino acid | Code |
|---|---|
| D-N-methyllysine | Dnmlys |
| N-methylcyclohexylalanine | Nmchexa |
| D-N-methylornithine | Dnmorn |
| N-methylglycine | Nala |
| N-methylaminoisobutyrate | Nmaib |
| N-(1-methylpropyl)glycine | Nile |
| N-(2-methylpropyl)glycine | Nile |
| N-(2-methylpropyl)glycine | Nleu |
| D-N-methyltryptophan | Dnmtrp |
| D-N-methyltyrosine | Dnmtyr |
| D-N-methylvaline | Dnmval |
| γ-aminobutyric acid | Gabu |
| L-t-butylglycine | Tbug |
| L-ethylglycine | Etg |
| L-homophenylalanine | Hphe |
| L-α-methylarginine | Marg |
| L-α-methylaspartate | Masp |
| L-α-methylcysteine | Mcys |
| L-α-methylglutamine | Mgln |
| L-α-methylhistidine | Mhis |
| L-α-methylisoleucine | Mile |
| D-N-methylglutamine | Dnmgln |
| D-N-methylglutamate | Dnmglu |
| D-N-methylhistidine | Dnmhis |
| D-N-methylisoleucine | Dnmile |
| D-N-methylleucine | Dnmleu |
| D-N-methyllysine | Dnmlys |
| N-methylcyclohexylalanine | Nmchexa |
| D-N-methylornithine | Dnmorn |
| N-methylglycine | Nala |
| N-methylaminoisobutyrate | Nmaib |
| N-(1-methylpropyl)glycine | Nile |
| N-(2-methylpropyl)glycine | Nleu |
| D-N-methyltryptophan | Dnmtrp |
| D-N-methyltyrosine | Dnmtyr |
| D-N-methylvaline | Dnmval |
| γ-aminobutyric acid | Gabu |
| L-t-butylglycine | Tbug |
| L-ethylglycine | Etg |
| L-homophenylalanine | Hphe |
| L-α-methylarginine | Marg |
| L-α-methylaspartate | Masp |
| L-α-methylcysteine | Mcys |
| L-α-methylglutamine | Mgln |
| L-α-methylhistidine | Mhis |
| L-α-methylisoleucine | Mile |
| L-α-methylleucine | Mleu |
| L-α-methylmethionine | Mmet |
| L-α-methylnorvaline | Mnva |
| L-α-methylphenylalanine | Mphe |
| L-α-methylserine | mser |
| L-α-methylvaline | Mtrp |
| L-α-methylleucine | Mval Nnbhm |
| N-(N-(2,2-diphenylethyl)carbamylmethyl-glycine | Nnbhm |
| 1-carboxy-1-(2,2-diphenylethylamino)cyclopropane | Nmbc |
| L-N-methylalanine | Nmala |
| L-N-methylarginine | Nmarg |
| L-N-methylasparagine | Nmasn |
| L-N-methylaspartic acid | Nmasp |
| L-N-methylcysteine | Nmcys |
| L-N-methylglutamine | Nmgin |
| L-N-methylglutamic acid | Nmglu |
| L-N-methylhistidine | Nmhis |
| L-N-methylisolleucine | Nmile |
| L-N-methylleucine | Nmleu |
| L-N-methyllysine | Nmlys |
| L-N-methylmethionine | Nmmet |
| L-N-methylnorleucine | Nmnle |
| L-N-methylnorvaline | Nmnva |
| L-N-methylornithine | Nmorn |
| L-N-methylphenylalanine | Nmphe |
| L-N-methylproline | Nmpro |
| L-N-methylserine | Nmser |
| L-N-methylthreonine | Nmthr |
| L-N-methyltryptophan | Nmtrp |
| L-N-methyltyrosine | Nmtyr |

TABLE 4-continued

Non-conventional or modified amino acids.

| Non-conventional amino acid | Code |
|---|---|
| L-N-methylvaline | Nmval |
| L-N-methylethylglycine | Nmetg |
| L-N-methyl-t-butylglycine | Nmtbug |
| L-norleucine | Nle |
| L-norvaline | Nva |
| α-methyl-aminoisobutyrate | Maib |
| α-methyl-γ-aminobutyrate | Mgabu |
| α-methylcyclohexylalanine | Mchexa |
| α-methylcyclopentylalanine | Mcpen |
| α-methyl-α-napthylalanine | Manap |
| α-methylpenicillamine | Mpen |
| N-(4-aminobutyl)glycine | Nglu |
| N-(2-aminoethyl)glycine | Naeg |
| N-(3-aminopropyl)glycine | Norn |
| N-amino-α-methylbutyrate | Nmaabu |
| α-napthylalanine | Anap |
| N-benzylglycine | Nphe |
| N-(2-carbamylethyl)glycine | Ngln |
| N-(carbamylmethyl)glycine | Nasn |
| N-(2-carboxyethyl)glycine | Nglu |
| N-(carboxymethyl)glycine | Nasp |
| N-cyclobutylglycine | Ncbut |
| N-cycloheptylglycine | Nchep |
| N-cyclohexylglycine | Nchex |
| N-cyclodecylglycine | Ncdec |
| N-cyclododeclglycine | Ncdod |
| N-cyclooctylglycine | Ncoct |
| N-cyclopropylglycine | Ncpro |
| N-cycloundecylglycine | Ncund |
| N-(2,2-diphenylethyl)glycine | Nbhm |
| N-(3,3-diphenylpropyl)glycine | Nbhe |
| N-(3-indolylyethyl)glycine | Nhtrp |
| N-methyl-γ-aminobutyrate | Nmgabu |
| D-N-methylmethionine | Dnmmet |
| N-methylcyclopentylalanine | Nmcpen |
| D-N-methylphenylalanine | Dnmphe |
| D-N-methylproline | Dnmpro |
| D-N-methylserine | Dnmser |
| D-N-methylserine | Dnmser |
| D-N-methylthreonine | Dnmthr |
| N-(1-methylethyl)glycine | Nva |
| N-methyla-napthylalanine | Nmanap |
| N-methylpenicillamine | Nmpen |
| N-(p-hydroxyphenyl)glycine | Nhtyr |
| N-(thiomethyl)glycine | Ncys |
| penicillamine | Pen |
| L-α-methylalanine | Mala |
| L-α-methylasparagine | Masn |
| L-α-methyl-t-butylglycine | Mtbug |
| L-methylethylglycine | Metg |
| L-α-methylglutamate | Mglu |
| L-α-methylhomo phenylalanine | Mhphe |
| N-(2-methylthioethyl)glycine | Nmet |
| N-(3-guanidinopropyl)glycine | Narg |
| N-(1-hydroxyethyl)glycine | Nthr |
| N-(hydroxyethyl)glycine | Nser |
| N-(imidazolylethyl)glycine | Nhis |
| N-(3-indolylyethyl)glycine | Nhtrp |
| N-methyl-γ-aminobutyrate | Nmgabu |
| D-N-methylmethionine | Dnmmet |
| N-methylcyclopentylalanine | Nmcpen |
| D-N-methylphenylalanine | Dnmphe |
| D-N-methylproline | Dnmpro |
| D-N-methylserine | Dnmser |
| D-N-methylthreonine | Dnmthr |
| N-(1-methylethyl)glycine | Nval |
| N-methyla-napthylalanine | Nmanap |
| N-methylpenicillamine | Nmpen |
| N-(p-hydroxyphenyl)glycine | Nhtyr |
| N-(thiomethyl)glycine | Ncys |
| penicillamine | Pen |
| L-α-methylalanine | Mala |
| L-α-methylasparagine | Masn |
| L-α-methyl-t-butylglycine | Mtbug |
| L-methylethylglycine | Metg |
| L-α-methylglutamate | Mglu |
| L-α-methylhomophenylalanine | Mhphe |
| N-(2-methylthioethyl)glycine | Nmet |
| L-α-methyllysine | Mlys |
| L-α-methylnorleucine | Mnle |
| L-α-methylornithine | Morn |
| L-α-methylproline | Mpro |
| L-α-methylthreonine | Mthr |
| L-α-methyltyrosine | Mtyr |
| L-N-methylhomophenylalanine | Nmhphe |
| N-(N-(3,3-diphenylpropyl)carbamylmethyl(1)glycine | Nnbhe |

Thus, the method of the present invention can be used to kill with optimal efficaciousness, rapidity and selectivity essentially any target cell/tissue displaying a specific surface marker, and hence can be used to treat in a subject essentially any such disease with optimal effectiveness, rapidity and safety, as demonstrated in the Examples section below, with respect to glioblastoma, the most malignant, intractable and lethal form of human brain cancer.

As described hereinabove, the composition-of-matter of the present invention may be used per se or as an active ingredient in a pharmaceutical composition.

As used herein a "pharmaceutical composition" refers to a preparation of one or more of the active ingredients described herein with other chemical components such as physiologically suitable carriers and excipients. The purpose of a pharmaceutical composition is to facilitate administration of active ingredients to an organism.

Herein the term "active ingredients" refers to the composition-of-matter accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered active ingredients. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, transnasal, intestinal or parenteral delivery, including intramuscular, subcutaneous and intramedullary injections as well as intrathecal, direct intraventricular, intravenous, inrtaperitoneal, intranasal, intraocular or intra-cranial injection.

Alternately, as described hereinabove, one may administer the pharmaceutical composition in a local rather than systemic manner, for example, via injection of the pharmaceutical composition directly into a tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active ingredients with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active ingredient doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichlorotetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the active ingredients and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredients may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (composition-of-matter) effective to prevent, alleviate or ameliorate symptoms of a disorder (e.g., ischemia) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in-vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in-vitro, in cell cultures or experimental animals. The data obtained from these in-vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide plasma or brain levels of the active ingredients are sufficient to achieve target cell/tissue killing (minimal effective concentration, MEC). The MEC will vary for each preparation, but can be estimated from in-vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredients. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3;996,345; 4,034,074; 4,098,876; 4,879,219; 5,011,771 and 5,281,521, "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

Example 1

Optimally Efficient, Rapid and Selective dsRNA-mediated Killing of Glioblastoma Cells/Tissue Background: Diseases characterized by cells/tissue displaying a specific cell surface marker include numerous diseases, such as epidermal growth factor receptor (EGFR) overexpressing glioblastoma multiforme, having tremendous economic and medical repercussions for which no satisfactory treatment is available. An optimal strategy for selectively killing cells/tissue displaying a specific surface marker, such as malignant glioma cells/tissue, would be via dsRNA, an optimally small and cytotoxic compound capable of optimally penetrating highly dense viral vector-impermeable tumor tissue, such as glioblastoma tissue, and inducing apoptosis of tumors cells located deep within. While various prior art approaches have attempted to use dsRNA for selectively killing cells displaying a specific surface marker, all such approaches suffer from various critical disadvantages, including suboptimal efficacy, safety, and/or selectivity. While reducing the present invention to practice, as described below, a method of effectively, safely and selectively killing cells/tissues displaying a specific surface marker in-vivo was unexpectedly uncovered, thereby overcoming the limitations of the prior art.

Materials and Methods:

Selective transfection of cells displaying a specific surface marker, namely epidermoid, rectal, or renal carcinoma cells overexpressing epidermal growth factor receptor (EGFR), using complexation of a DNA expression vector with covalently coupled polyethylenimine (PEI)-epidermal growth factor (EGF) carrier, or with covalently coupled PEI-EGF-poly(ethylene glycol) (PEG) carrier has recently been reported (Ogris, M. et al., 2001. AAPS PharmSci 3:E21). These studies showed that incorporation of EGF in the carrier resulted in an up to 300-fold increase in transfection efficiency in tumor cells displaying epidermal growth factor receptor (EGFR). Such observations formed the basis of the following protocols which describe a method of producing double stranded RNA (dsRNA) complexed with an EGF-conjugated carrier and using transfection with such complex for optimally efficacious, rapid and selective killing of EGFR positive glioblastoma cells in-vitro and tissue in-vivo.

Cell lines: Cell lines employed include the human glioblastoma cell line U87MG, its derivative U87MGwtEGFR which overexpresses wild type EGF receptor (EGFR), and its derivative thereof U87MGΔEGFR which expresses Δ(2-7) EGFR, an EGFR mutant having a truncated extracellular domain incapable of specifically binding EGF. Cell lines U87MG, U87MGwtEGFR, and U87MGΔEGFR have previously been described (Shir A, and Levitzki A., 2002. Nat Biotechnol. 20, 895-900).

Lentiviral vectors and transfection: Green fluorescent protein (GFP)-encoding lentiviral vector was generated by transient cotransfection of vector SIN-PGK with plasmids pMD.G and pCMVDR8.91 (Zufferey, R. et al., 1997. Nat. Biotechnol. 15, 871-5) into the 293T cell line as previously described (Naldini, L. et al., 1996. Science 272, 263-7). Vector SIN-PGK vector encodes GFP under PGK promoter regulation, enabling convenient calculation of viral titer and infection efficiency via fluorescent microscopic or FACS analysis of infected cells.

pIC:carrier complex components: Double stranded RNA (dsRNA) in the form of a synthetic polyinosinic acid-polycytidylic acid complex (pIC) having RNA strands 100-300 ribonucleotides in length was obtained from Pharmacia-Amersham. FuGENE6 transfection reagent was obtained from Roche. Covalently conjugated polyethylenimine (PEI)$_{25}$-poly(ethylene glycol) (PEG)-epidermal growth factor (EGF) and PEI$_2$-melittin (MEL) dsRNA carriers were synthesized as described below.

Preparation of Covalently Conjugated PEI$_{25}$-PEG-EGF Carrier:

General guidance for preparing covalently conjugated PEI$_{25}$-PEG-EGF carrier is provided in Current Protocols In Human Genetics, Supplement 11, Chapter: Vectors for Gene Therapy, 12.3.17; 12.3.18. John Wiley & Sons, Inc., 1996.

Reagents: Branched polyethylenimine (PEI) having an average molecular weight of 25 kDa as determined via light scattering (PEI$_{25}$) and Succinimidyl 3-(2-pyridyldithio)propionate (SPDP) were purchased from Sigma-Aldrich (Munich, Germany). N-hydroxysuccinimidyl polyethyleneglycol maleimide (NHS-PEG-MAL, molecular weight=3.4 kDa) was obtained from Nektar Therapeutics (wwwdotnektardotcom). The compound NHS-PEG-MAL is used for conjugating moieties having a suitable reactive group to PEG. Recombinant mouse epidermal growth factor (EGF) was purchased from Pepro Tech EC Ltd. (London, UK).

Liquid chromatography: Liquid chromatography was performed using a Waters 626 pump and 996 diode array detector.

Quantitation of PEI: The PEI content of conjugates was determined spectrophotometrically via 2,4,6-trinitrobenzenesulfonic acid (TNBS) assay at 405 nm as previously described (Snyder, S. L., and Sobocinski, P. Z., 1975. Anal. Biochem. 64, 284-288).

Determination of the amount of dithiopyridine linkers: The amount of dithiopyridine linkers which could be generated in PEI$_{25}$ for conjugations was determined after reduction of an aliquot with dithiothreitol (DTT) followed by absorption measurement of released pyridine-2-thione at 343 nm (ε=8080/M cm).

Quantitation of reactive maleinimide groups in NHS-PEG-MAL: The amount of reactive maleinimide groups in NHS-PEG-MAL was calculated spectrophotometrically as a function of absorbance at 300 nm ($A_{300}$). A solution of 1 mg/ml NHS-PEG-MAL in water has an $OD_{300}$ of 0.15 for a 1 cm path length. The amount of the reactive maleinimide groups in the PEI$_{25}$-PEG-MAL conjugate were calculated similarly by the difference in $A_{300}$ prior to and following addition of 10 microliters 1 molar DTT solution to 100 microliters of the sample (addition of DTT removes the $A_{300}$ of the maleinimide group by electron delocalization).

Quantization of EGF concentration: The concentration of soluble recombinant EGF was calculated by measuring the absorption of EGF in solution at 280 nm: a solution of 1 mg/ml EGF in water results in an OD of 3.1 (1 cm path length).

The molar ratio of EGF and dithiopyridine in a EGF-PDP conjugate is determined spectrophotometrically at 280 and 340 nm. For the amount of dithiopyridine absorption is measured at 340 nm (see above). The initial absorption of the conjugate is measured at 280 nm ($A_{280}$); to correct for the absorption of dithiopyridine at 280 nm, this value is corrected by following equations.

$$A_{280\,a} = A_{340\,with\,DTTx}\,5.1/8.1. \qquad \text{Equation 1}$$

$$A_{280}\text{ revised} = A_{280} - A_{280\,a}. \qquad \text{Equation 2}$$

The result of equation 2 is used to calculate the final concentration of EGF.

An Ellman assay is used for the determination of the mercapto groups in EGF-SH, for example as previously described (Kousba A A, Poet T S, Timchalk C, 2003. Toxicology 188:219-32).

Synthesis of PEI$_{25}$PEG-MAL: A 1.6 micromole aliquot of PEI$_{25}$ obtained by gel-filtration (Sephadex G-25, superfine; Amersham Biosciences) dissolved in 0.25 M NaCl was adjusted to pH 4.4 by careful addition of HCl. A 6.4 micromole aliquot of NHS-PEG-MAL dissolved in 0.4 ml water was added, and after 1 hour reaction at room temperature the salt concentration was adjusted to 1 M NaCl. This mixture was loaded on a cation-exchange column (Macro-prep High S; 10/10; BioRad, München, Germany) and fractioned using a salt gradient of 1-3 M NaCl in 20 mM sodium acetate, pH 4.5 with a flow rate of 0.5 ml/minute. Fractionation was performed using Buffer A (20 mM sodium acetate pH 4.5) and Buffer B (3 M NaCl, 20 mM sodium acetate pH 4.5), as follows: Time=0-15 minutes: 56% Buffer A, 44% Buffer B; Time=15-20 minutes: 44-100% Buffer B; Time=20-60 minutes: 100% Buffer B. The detector was set to 240 and 300 nm, and the product was eluted at Time=40-50 minutes. The molar ratio of PEI$_{25}$ and reactive maleinimide groups was 1:1.6.

Synthesis of EGF-PDP: A 5 mg aliquot of EGF (molecular weight=6 kDa) was dialyzed overnight against 20 mM HEPES pH 7.1 (degassed with argon). A 0.5 micromole aliquot of EGF and a 5 micromole aliquot of succinimidyl 3-(2-pyridyldithio)propionate (SPDP; purchased from Sigma-Aldrich, München, Germany) from a 10 mM stock in 100% ethanol were mixed. The concentration of ethanol in the mixture was approximately 33% (v/v). After 3 hours at room temperature the reaction mixture was loaded on a gel-filtration column (G-10; HR10/30 column, Amersham Biosciences, Germany; 20 mM HEPES, pH 7.1 with 20% ethanol). The product (4 ml), detected at 300 nm, eluted at Time=18-26 min. The yield was 3.36 mg for EGF modified with 0.77 micromoles dithiopyridine.

Synthesis of EGF-SH: A 0.56 micromolar aliquot of EGF was mixed with 50 equivalents of DTT in 100 microliters of water. After 5 minutes at room temperature, the reaction mixture was loaded on a gel-filtration column (G-10; HR10/30 column, Amersham Biosciences, Germany; 20 mM HEPES, pH 7.1 with 20% ethanol). The product (5.5 ml), detected at 280 nm, was eluted at Time=17-28 minutes. The molar ratio of EGF to —SH groups was 1:1.82.

Synthesis of $PEI_{25}PEG$-EGF: A 0.28 micromolar aliquot of EGF containing 0.51 micromoles of thiol groups was mixed under argon with $PEI_{25}$-PEG-MAL containing 0.51 micromoles of reactive maleinimide groups. The final pH of the reaction mixture was 6, and the final salt concentration was 0.3 M NaCl. After a 26 hour incubation at room temperature the salt concentration of the reaction mixture was adjusted to 0.5 M with 3 M NaCl, the reaction mixture was loaded on a cation-exchange column (Macro-prep High S; 10/10; BioRad, München, Germany) and fractioned with a salt gradient of 0.5-3M NaCl in 20 mM HEPES, pH 7.1 using a flow rate of 0.5 ml/minute and the detector set at 280 nm. Fractionation was performed using Buffer A (20 mM HEPES pH 7.1) and Buffer B (20 mM HEPES pH 7.1, 3 M NaCl), as follows: Time=0-20 minutes: 78% Buffer A, 22% Buffer B; Time=20-80 minutes: 22-100% Buffer B; Time=80-90 minutes: 100% Buffer B. The conjugate was eluted at 2.4-3 M NaCl (10 ml pooled). Fractions (Time=10-28 minutes, product B) in the isocratic part were also pooled (9 ml). The product was dialyzed overnight at 4° C. against HBS buffer (20 mM HEPES pH 7.1, 150 mM NaCl), pH 7.3 (degassed with argon). The amount of EGF in the conjugate (0.65 mg) and in product B (0.98 mg) was determined spectrophotometrically at 280 nm. The concentration of $PEI_{25}$ in the conjugate (136 nmol) and in product B (38 nmol) was determined spectrophotometrically by TNBS assay at 405 nm. The molar ratio of EGF to $PEI_{25}$ in the conjugate was 0.8:1.

Preparation of $PEI_2$-Mel Conjugate Carrier:

Reagents and Assays:

Polyethylenimine having a molecular weight of 2 kDa ($PEI_2$) and Succinimidyl 3-(2-pyridyldithio)propionate (SPDP) were purchased from Sigma-Aldrich (München, Germany). The compound D-Mel-SH (molecular weight=2893.6) comprising the peptide melittin (Mel) having the amino acid sequence CIGAVLKVLTTGLPAL-ISWIKRKRQQ (SEQ ID NO: 1) was obtained from Dr. Arnold, Gene-Center of the University of Munich.

Liquid chromatography of conjugates: Liquid chromatography of conjugates was performed with the Amersham-Biosciences ÄKTA-System. The PEI content of the conjugate was determined spectro photometrically by TNBS assay at 405 nm. The melittin content was determined via the extinction coefficient (e280 nm=5,570). The amount of dithiopyridine linkers available in $PEI_2$ for conjugation was determined after reduction of an aliquot with dithiothreitol (DTT) followed by absorption measurement of released pyridine-2-thione at 343 nm.

Synthesis of $PEI_2PDP$: A 10 micromole aliquot of $PEI_2$ from a 100 mg/ml $PEI_2$ stock solution was adjusted to pH 7.1 with HCl, mixed with 20 micromoles of SPDP dissolved in 0.2 ml dimethylsulfoxide (DMSO) and the volume was adjusted to 1 ml with 250 mM NaCl/50 mM HEPES pH 7.1. The mixture was incubated at room temperature for 2 hours and subsequently loaded on a gel-filtration column (Sephadex G-10; HR10/30 column, Amersham Biosciences, Germany; 1/10 HBS [15 mM NaCl, 2 mM HEPES pH 7.1]). The product eluted at Time=8-10 min (3 ml). A 1 ml sample of product containing 11 mg of $PEI_2$ (5.5 mM) and 5.52 mM dithiopyridine linker was obtained.

Synthesis of $PEI_2Mel$: A 7 mg aliquot of D-Mel-SH was dissolved in 100 mM HEPES pH 7.4, 500 M NaCl (buffer degassed with argon) and mixed with a 25% excess of PDP (3.03 mol PDP=6.06 g $PEI_2$-PDP). After 4 hours under argon the reaction mixture was loaded on a cation-exchange column (Macro-prep High S; BioScale 2 1; BioRad, München, Germany) and fractioned with a salt gradient of 0.5-3 M NaCl in 20 M HEPES pH 7.1. The product (20 ml) eluted at 1.45-3 M NaCl. The $PEI_2$-Mel conjugate was dialyzed against 4 L of 1/10 HBS pH 7.1 (argon degassed) overnight, concentrated to 1 ml with a speed vac and sterile-filtered. The final concentrations in the conjugate were 2.23 mM for $PEI_2$, 1.75 mM for the remaining PDP groups and 2.09 mM for melittin.

Formation of pIC:carrier complexes and transfection: A 1 microgram aliquot of pIC was dissolved in 25 microliters HBS buffer as was 0.78 microgram of $PEI_{25}$-PEG-EGF or 0.08 microgram of $PEI_{25}$-PEG-EGF+0.7 microgram of $PEI_2$-Mel. The carriers were mixed with the pIC by pipetting to generate pIC:$PEI_{25}$-PEG-EGF+$PEI_2$-Mel complex. Carrier for larger amounts of pIC was prepared proportionally. Thirty minutes later culture medium supernatant of cells to be transfected was exchanged with culture medium supplemented with pIC:carrier complex so as to transfect the cells with the required carrier complex concentration.

Interferon (IFN)-α assay: Cellular secretion of interferon (IFN)-α by tumor cells transfected with pIC:carrier complex was measured via IFN-α ELISA (IBL, Germany).

In-vivo assays: For analysis of efficiency of infection of glioblastoma tumor tissue by viral vectors, U87MGΔEGFR cells were injected subcutaneously into nude mice. Two weeks later tumors having an average volume of 274 cubic millimeters were established and direct single infection of the tumors with 50 microliters of concentrated GFP expressing lentiviral vector ($10^9$ IU/ml) was performed. Forty-eight hours following transfection the animals were sacrificed, tumors were excised and ultra-thin cuts of the excised tumors were analyzed. The distribution of the infected cells and infection efficiency were calculated by visualization of the GFP expressing cells via fluorescent confocal microscopy.

For analysis of efficiency of anti tumor activity of dsRNA: carrier complex, $10^4$ U87MGwtEGFR cells were implanted intracranially in 35 nude mice, as previously described by the present inventors (Shir and Levitzki, 2002. Nat Biotech. 20:895) and the implanted cells were left to generate a tumor for 10 days. On day 10 post implantation, using 200 microliter Alzet osmotic micropumps with intratumoral catheters, pIC:$PEI_{25}$-PEG-EGF+$PEI_2$-Mel complex dissolved in HBG buffer (Ogris et al., 2001. J Biol Chem. 276:47550-5) was delivered directly into tumors of mice at a constant rate of 0.1 microgram pIC per 0.8 microliter per hour for 3 days (19.2 micrograms/day). The pumps were replaced every 12 hours. As negative controls, control mice received HBG buffer only, or were left untreated. Evaluation of tumor size was performed as previously described (Mishima et al., 2001. Cancer Res. 61:5349-54). Animal experiments were conducted in accordance with the Hebrew University guidelines for the care of laboratory animals.

Figure 2:
FIG. 2 is a fluorescence photomicrograph depicting 100% infection efficiency of lentiviral vector encoding green fluorescent protein (GFP) when infecting U87MG cells in-vitro.

Experimental Results:

Comparison of In-Vivo and In-Vitro Infection Efficiency of the Lentiviral Vectors:

Determination of infection efficiency of glioblastoma cells with lentiviral vector in-vitro: In order to determine infection efficiency of lentiviral vector in-vitro, $10^5$ U87MG cells were seeded in a volume of 2 ml medium per well in 6-well plates and grown overnight. The cells were then infected with $2\times10^5$ IU of lentiviral vector encoding green fluorescent protein (GFP) marker. Forty-eight hours after infection transfected cells were photographed using a fluorescent microscope with digital camera, numbers of GFP positive cells were scored and transfection efficiency was calculated. The percentage of infected cells was also calculated by FACS analysis (data not shown). As shown in FIG. 2, the lentiviral vectors infected glioblastoma cells in-vitro with an efficiency of 100%.

Figure 3A:
FIGS. 3a-f are a fluorescent photomicrograph-schematic diagram combination graphic depicting very low infection efficiency of GFP-expressing lentiviral vector when transfecting glioblastoma tumor in-vivo in nude mice. Cryostat sections from the tumor tissue, as indicated, were analyzed for expression of GFP by confocal microscopy.
Figure 3B:
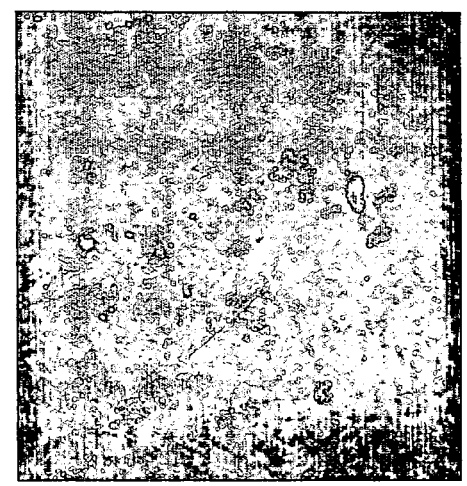
Figure 3C:
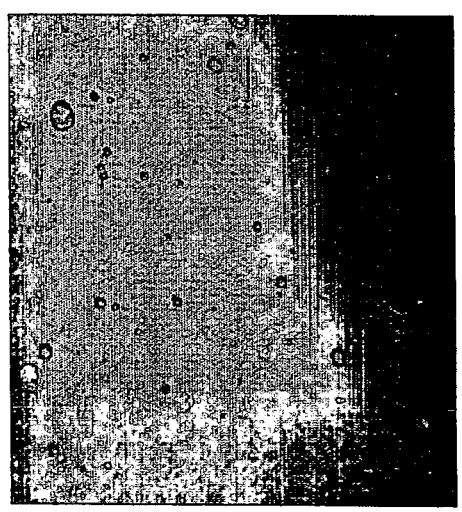
Figure 3D:
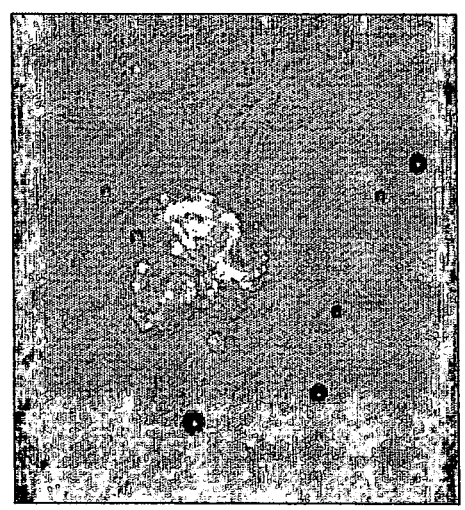
Figure 3E:
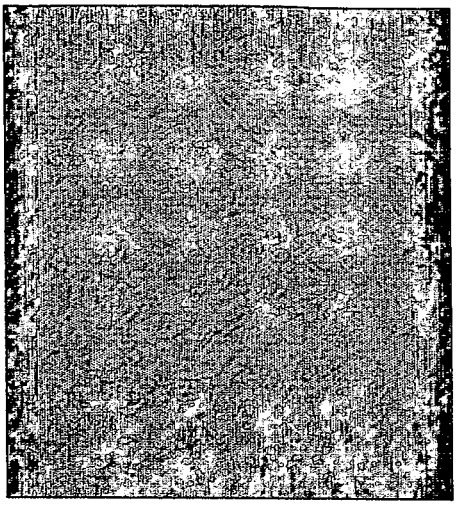
Figure 3F:
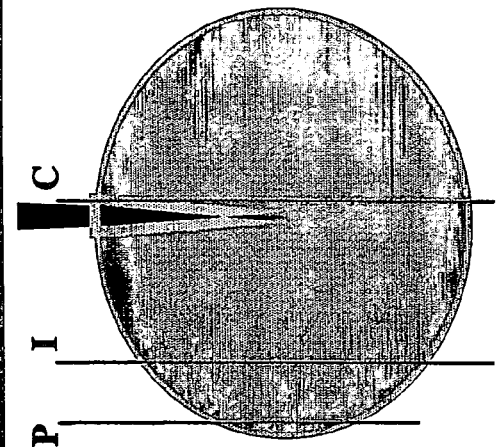

Very low infection efficiency of glioblastoma tumor tissue with lentiviral vector in-vivo: To test infection efficiency of lentiviral vector in tumors established in-vivo, $10^6$ U87MGΔEGFR cells were injected subcutaneously into nude mice. Two weeks later tumors having an average volume of 274 cubic millimeters were established and direct single infection of the tumors with 50 microliters of concentrated GFP expressing lentiviral vector ($10^9$ IU/ml) was performed. Forty-eight hours following transfection the animals were sacrificed, tumors were excised and ultra-thin cuts were performed. The distribution of the infected cells and infection efficiency were calculated by visualization of the GFP expressing cells through fluorescent confocal microscopy (FIGS. 3a-f). All infected cells were found to be located in the periphery (FIGS. 3a-b) and center of the tumor (FIGS. 3c-d) of the tumor, namely the areas of direct exposure of the cells to virus, while cells in intermediate areas (over 99% of the tumor) were uninfected (FIG. 3e). A schematic diagram of the sectioning scheme is depicted in FIG. 3f. These results led to the conclusion that low in-vivo infection efficiency is a result of low percentage of the cells exposed to the virus.

Three-fold higher levels of glioblastoma cell killing in-vitro mediated by pIC:PEI$_{25}$ or pIC:FuGENE6 complex: Transfection of U87MG glioblastoma cells with various amounts of pIC double stranded RNA (dsRNA) with PEI$_{25}$ or FuGENE6 transfection reagent (Roche) resulted in death of up to 92% of U87MG cells (FIGS. 4a and 4b, respectively) 1 hour following transfection. Transfection with PEI$_{25}$ in medium supplemented with serum was found to be inefficient. The average transfection efficiency of either β-galactosidase or GFP encoding plasmid into glioblastoma cells was previously determined to be 30% by FuGENE6 mediated plasmid transfection (Shir, A. and Levitzki, A., 2002. Nat Biotechnol 20, 895-900). Thus, the observed 92% efficiency of dsRNA induced cell death is at least 3 times higher than the maximum efficiency of cell death induced by plasmid transfection.

Figure 6:
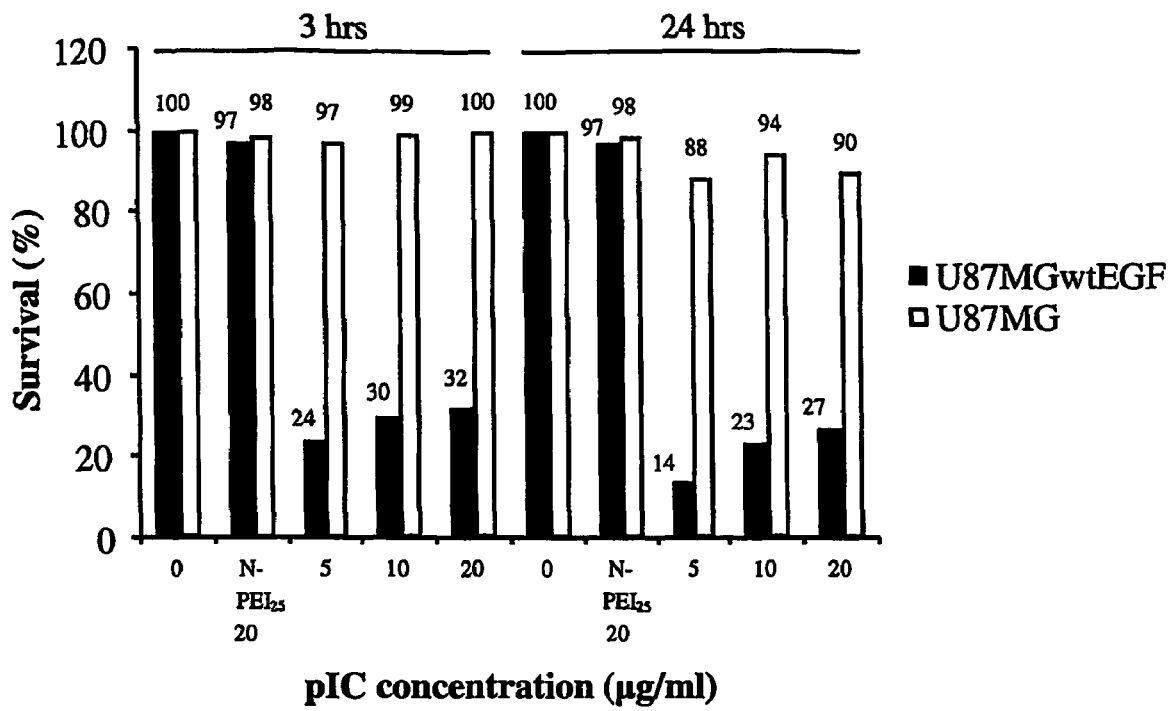
FIG. 6 is a bar graph depicting high death rates of U87MGwtEGFR cells 3 and 24 hours following transfection with pIC:PEI$_{25}$-PEG-EGF complex. Aliquots of 5,000 cells in a volume of 200 microliters medium were seeded per well in 96-well plates, and grown overnight. The cells were then transfected with pIC at the indicated concentration in complex with PEI$_{25}$-PEG-EGF carrier. Cell viability was assessed 3 and 24 hours following transfection via methylene blue assay. Numbers above bars denote percent cell survival.

High apoptotic death rates of wild type EGFR overexpressing glioblastoma cells 1 hour posttransfection with pIC: PEI$_{25}$PEG-EGF complex: Transfection of U87MGwtEGFR cells with pIC:PEI$_{25}$-PEG-EGF complex resulted in high apoptotic death rates one hour following transfection, as determined via Annexin and Tunel assays (FIGS. 5a and 5b, respectively). No significant effect was observed on growth of control U87MG cells at the dose range examined. Up to 76% of U87MGwtEGFR cells were killed within 3 hours after transfection (FIG. 6: 5 micrograms/ml pIC) with no significant effect on the growth of U87MG cells. Twenty-four hours following transfection the death rate of the U87MG.wtEGFR cells transfected with 5 micrograms/ml of pIC was 86% compared to only 12% of control U87MG cells. Optimal results were obtained using a per weight ratio of dsRNA to PEI$_{25}$ in 25 microliters HBS buffer (20 mM HEPES pH 7.1, 150 mM NaCl) of 1:0.78. The ratio of nitrogen in PEI$_{25}$ to phosphate in nucleic acids is usually 6. Dilution of the complex in a lower volume of buffer resulted in lower effect despite higher amounts of pIC used.

Figure 7:
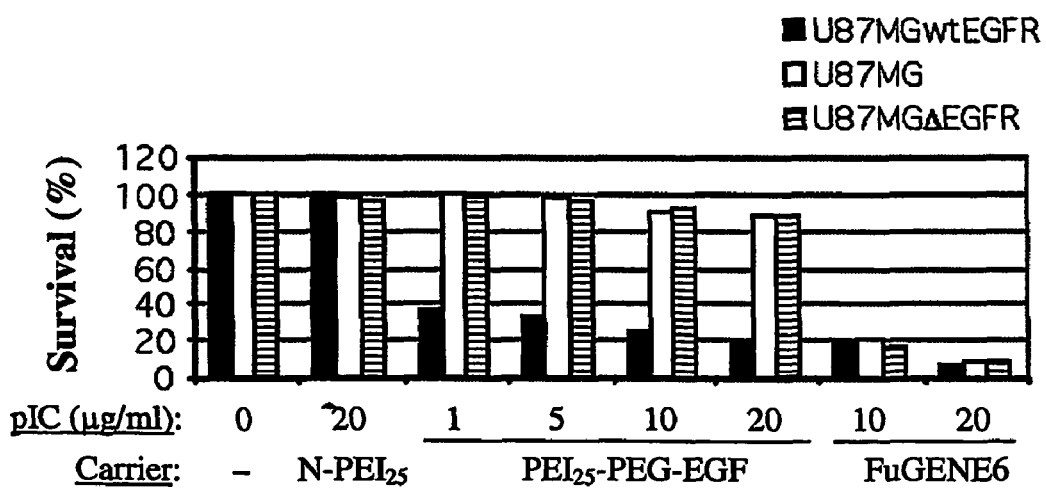
FIG. 7 is a bar-graph depicting the capacity of pIC:PEI$_{25}$-PEG-EGF complex to specifically and efficiently kill U87MGwtEGFR malignant glioma cells which display wild type EGFR but not malignant glioma cells which do not display any form of EGFR or which display Δ(2-7) EGFR only. Cells were grown and transfected to express the indicated EGFR, transfected with pIC at the indicated concentration in complex with the indicated carrier, and percent survival was assayed 24 hours posttransfection via methylene blue assay.

Highly efficient and specific killing of glioblastoma cells overexpressing wild type EGFR by transfection with pIC: PEI$_{25}$-EGF-PEG complex. As shown in FIG. 7, transfection with pIC:PEI$_{25}$-PEG-EGF complex was found to be capable of killing U87MGwtEGFR cells with high efficiency and specificity, as evidenced by the virtual absence of effect on either U87MG and U87MGΔEGFR cells which do not display any EGFR, or which display Δ(2-7) EGFR, respectively.

Figure 8:
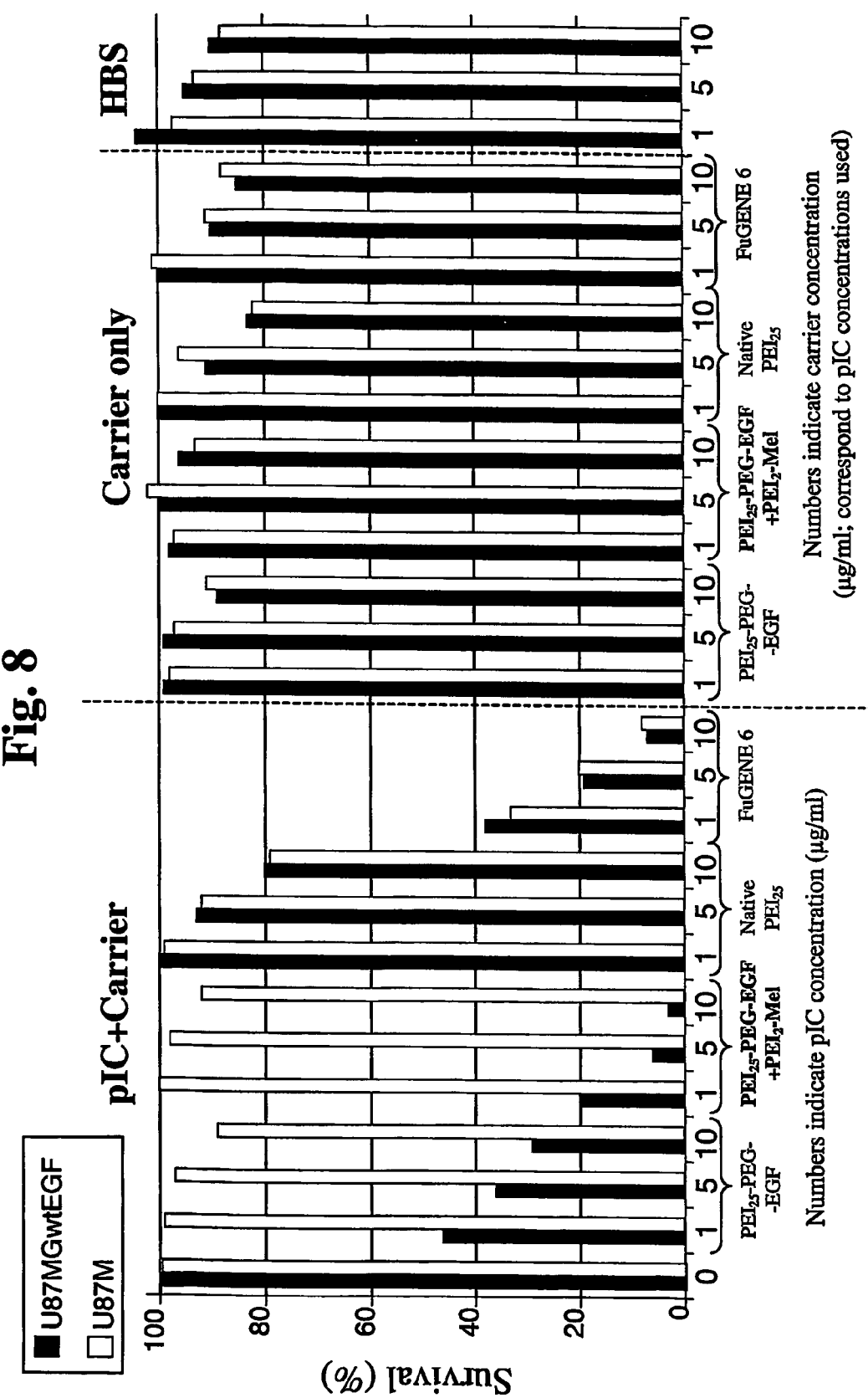
FIG. 8 is a histogram depicting enhanced cell killing effect of pIC:PEI$_{25}$-PEG-EGF complex by partial replacement of PEI$_{25}$-PEG-EGF carrier in complex with PEI$_2$-Mel carrier. U87MG-wtEGFR cells were transfected with pIC complexed with either PEI$_{25}$-PEG-EGF or PEI$_{25}$-PEG-EGF+PEI$_2$-Mel carrier at a ratio of PEI$_{25}$-PEG-EGF to PEI$_2$-Mel of 1:10. The effect was measured by methylene blue assay 24 hours following transfection.

Incorporation of PEI$_2$-Mel carrier enhances cytotoxicity of pIC:PEI$_{25}$-PEG-EGF complex in wild type EGFR overexpressing target glioblastoma cells: The cell killing effect was enhanced dramatically, yet remained highly selective, when PEI$_2$-Mel carrier was incorporated into pIC:PEI$_{25}$-PEG-EGF complex (FIG. 8; pIC:PEI$_{25}$-PEG-EGF+PEI$_2$-Mel). Melittin is a bee venom peptide which activates phospholipase A2, an event associated with disruption of endosomal membrane. Hence, the cytotoxic enhancement observed by incorporation of PEI$_2$-Mel carrier into pIC:carrier complex may be mediated by facilitating release of dsRNA from endosome to cytoplasm, as previously suggested (Ogris, M. et al. AAPS PharmSci 2001. 3(3) article 21). Such enhancement may also be associated with the reported capacity of RNA to disaggregate more easily from PEI$_2$ than from higher molecular weight PEI (Ogris, M. et al. AAPS PharmSci 2001. 3(3) article 21) which would enhance release of PEI$_2$ complexed pIC to the cytoplasm relative to PEI$_{25}$ complexed pIC. Hence, using pIC:PEI$_{25}$-PEG-EGF+PEI$_2$-Mel mixed carrier complex it was possible to kill more than 95% of U87MGwtEGFR target cells with virtually no effect on control U87MG cells (FIG. 8). Furthermore, no significant cytotoxic effect of the carriers on either target cell line could be detected in the absence of pIC (FIG. 8).

Figure 9:
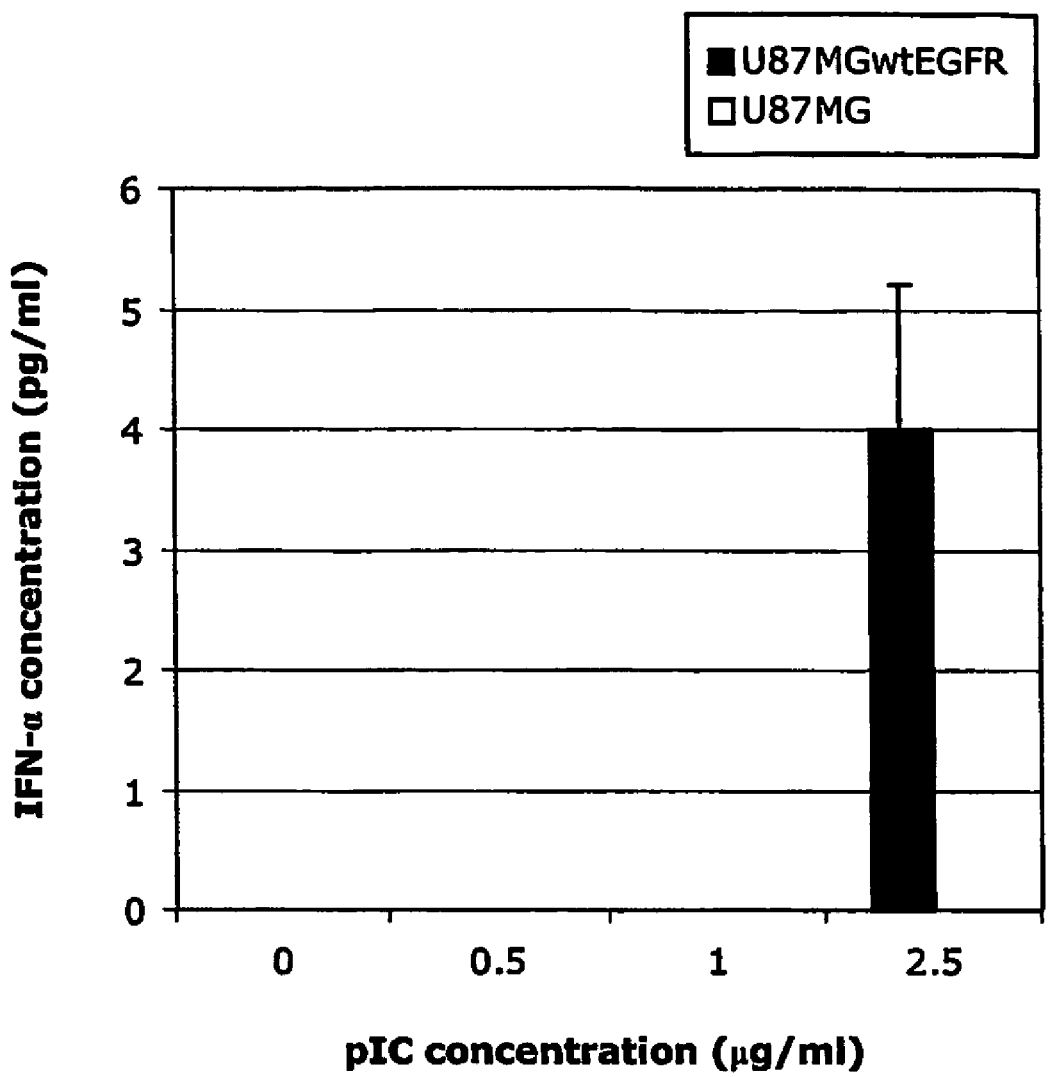
FIG. 9 is a bar graph depicting stimulation of IFN-α secretion specifically in U87MGwtEGFR cells following stimulation with pIC:PEI$_{25}$-PEG-EGF+PEI$_2$-Mel complex. Suspensions of 500,000 U87MG or U87MGwtEGFR cells were seeded in 6 cm plates and grown overnight, and transfected with pIC:PEI$_{25}$-PEG-EGF+PEI$_2$-Mel complex at the indicated pIC concentrations. Culture medium supernatant was harvested 24 hours posttransfection and analyzed for IFN-α content via ELISA.

EGFR overexpressing glioblastoma cells transfected with wild type pIC:PEI$_{25}$PEG-EGF+PEI$_2$-Mel complex specifically secrete IFN-α: Using ELISA, significant secretion of IFN-α in the medium by U87MGwtEGFR cells transfected with 2.5 micrograms/ml of pIC:PEI$_{25}$-PEG-EGF+PEI$_2$-Mel complex was measured 24 hours posttransfection (FIG. 9). No secretion of IFN-α was detected at lower or higher concentrations of pIC at longer or similar periods of time posttransfection (data not shown). No IFN-β expression could be detected at the pIC:PEI$_{25}$-PEG-EGF+PEI$_2$-Mel complex concentrations tested (data not shown).

Figure 10A:
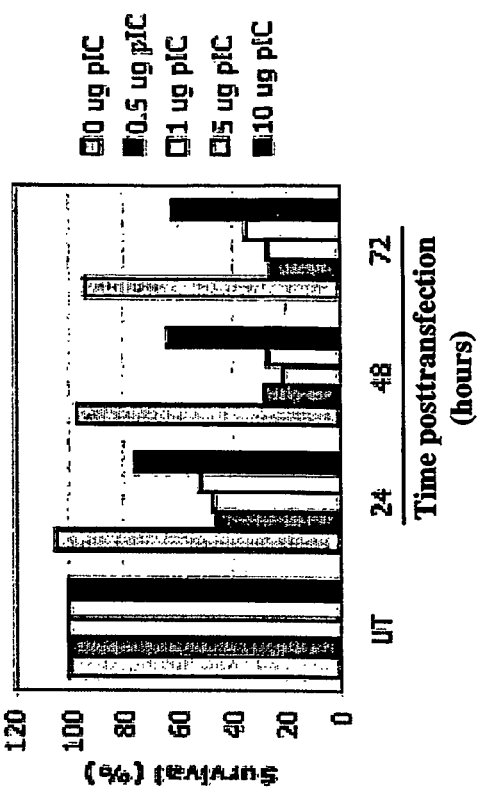
FIGS. 10a-d are histograms depicting secretion of soluble growth inhibitory factors by pIC:PEI$_{25}$-PEG-EGF+PEI$_2$-Mel complex transfected wild type EGFR overexpressing glioblastoma cells (bystander effect). For testing of bystander effect, aliquots of 4,000 U87MG (FIGS. 10a and 10c) or U87MGΔEGFR cells (FIGS. 10b and 10d) were seeded in 96-well plates and grown overnight in 200 microliters culture medium. Afterwards, 100 microliters of culture medium supernatant was exchanged with 100 microliters of culture medium conditioned by U87MGwtEGFR cells transfected with pIC:PEI$_{25}$-PEG-EGF+PEI$_2$-Mel complex harvested at the indicated times posttransfection. Cell proliferation was assessed 24 (FIGS. 10c-d) and 48 (FIGS. 10a-b) hours following medium exchange. For generation of conditioned medium suspensions of 500,000 U87MGwtEGFR cells were seeded in 6 cm plates, grown overnight in 2 ml culture medium, and transfected with pIC:PEI$_{25}$-PEG-EGF+PEI$_2$-Mel complex at the indicated pIC concentrations. UT—no medium exchange.
Figure 10B:
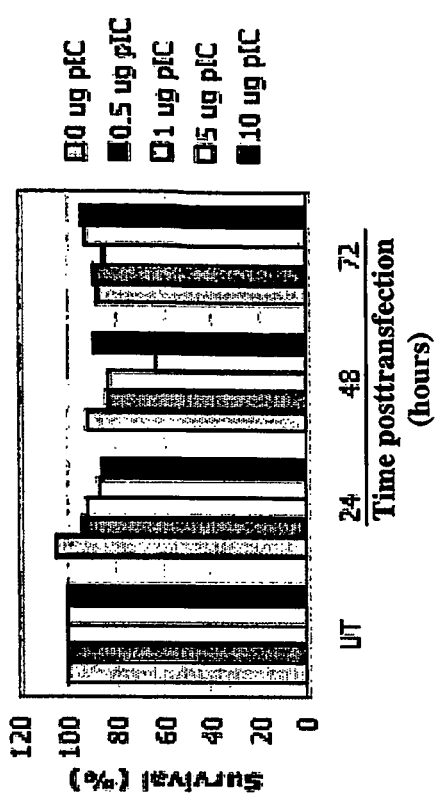
Figure 10C:
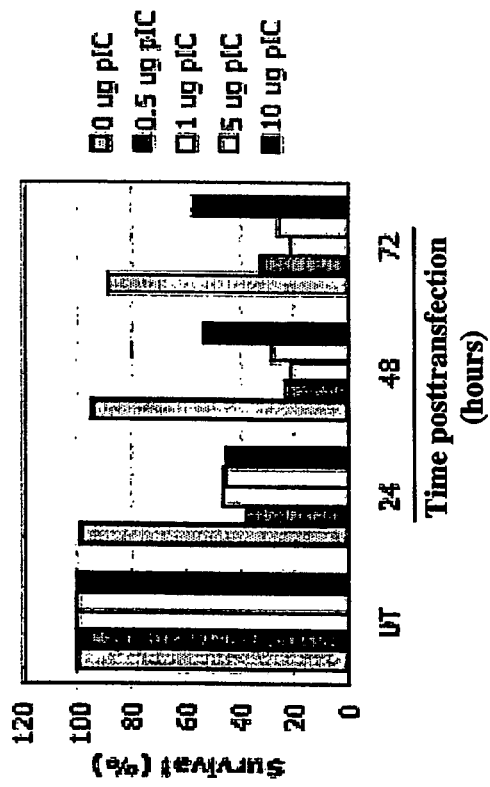
Figure 10D:
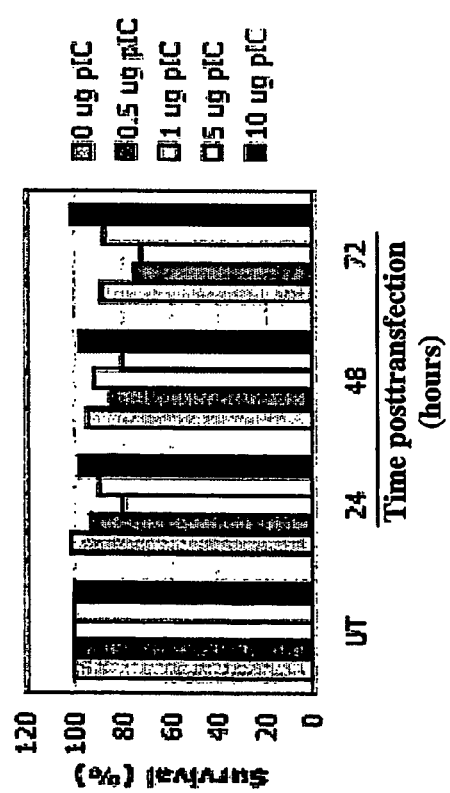
Figures 10E, 10F, 10G, 10H:
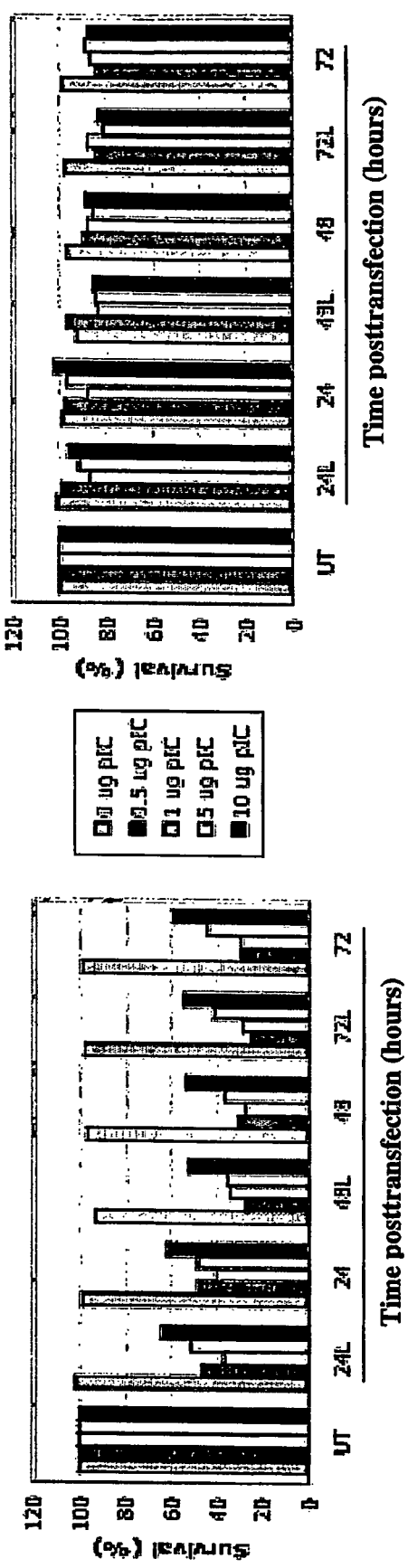
FIGS. 10e-h are histograms depicting that the growth inhibitory effect (bystander effect) of medium conditioned with pIC carrier complex transfected cells is not due to residual pIC:carrier complex used for transfection.

Wild type EGFR overexpressing glioblastoma cells transfected with pIC:PEI$_{25}$PEG-EGF+PEI$_2$-Mel complex secrete soluble growth inhibitory factors (bystander effect): FIGS. 10a-h show that medium conditioned by transfected U87MGwtEGFR cells contains soluble factors which significantly inhibits growth of U87MGwtEGFR, U87MG and U87MGΔEGFR cells not transfected with pIC:carrier complex. In order to verify that the growth inhibitory effect of the conditioned medium is not simply mediated by residual pIC: carrier complex used for transfection, the incapacity of treatment with lysate of EGFR overexpressing U87MGwtEGFR cells to abrogate the growth inhibitory activity of the conditioned medium was demonstrated (FIGS. 10e-f). Further control experiments demonstrated the capacity of treatment with such lysate to indeed inhibit the cytotoxic activity of the pIC:carrier complex (FIGS. 10g-h).

Figure 4A:
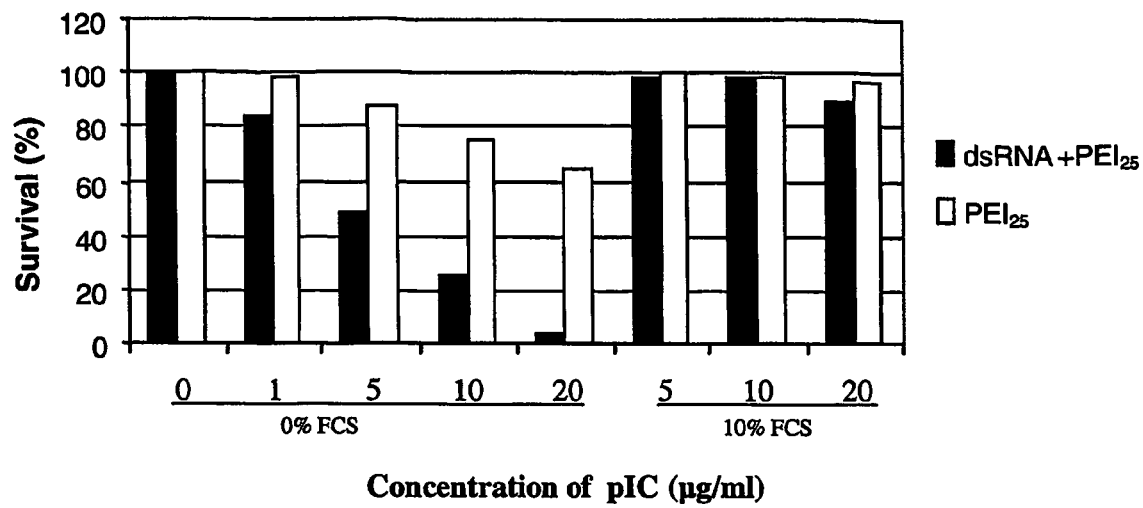
FIGS. 4a-b are bar graphs depicting high levels of U87MG glioblastoma cell killing in-vitro mediated by transfection with pIC:PEI$_{25}$ or pIC:FuGENE6 complex, respectively. Aliquots of 5,000 U87MG cells in a volume of 200 microliters of medium were seeded per well in 96-well plates, and grown overnight. The cells were then transfected with the indicated concentrations of pIC in complex with either native PEI$_{25}$ or FuGENE6 carrier. Transfections with PEI$_{25}$ were performed as previously described (Kircheis R. et al., 2001. Gene Therapy 8, 28-40). Transfection with FuGENE6 was performed according to the manufacturer's instructions.
Figure 4B:
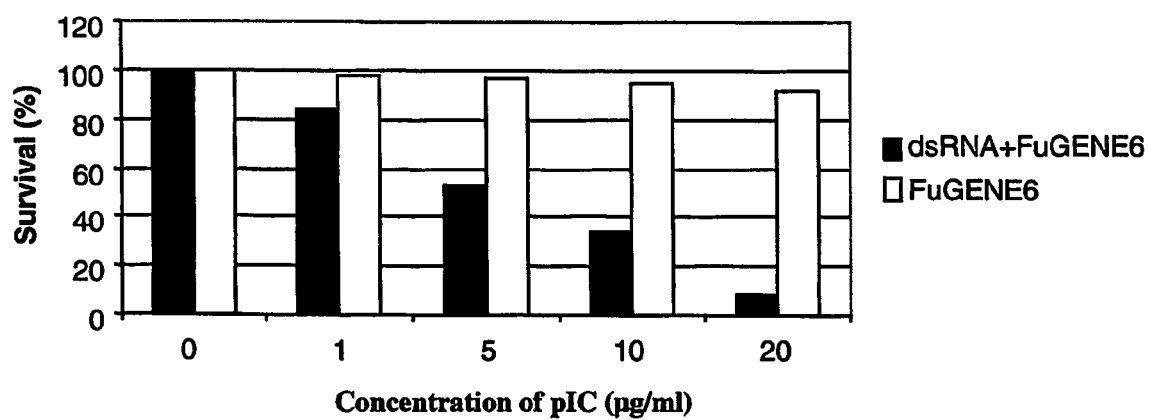

Treatment with pIC:PEI$_{25}$-PEG-EGF+PEI$_2$-Mel complex cures of mammals bearing wild type EGFR overexpressing human glioblastoma tumors: In order to determine whether pIC:PEI$_{25}$-PEG-EGF+PEI$_2$-Mel complex can be used to treat glioblastomal tumors in-vivo, mice were generated bearing 10 day old intracranial U87MGwtEGFR derived tumors, as shown in FIG. 11a. At this point, pIC:PEI$_{25}$-PEG-EGF+PEI$_2$-Mel complex was delivered intratumorally at a constant rate for 3 days. On day 20 after tumor inoculation, 7 days after the end of treatment with the dsRNA:carrier complex, tumors had disappeared completely in animals treated with the complex, while the tumor continued to grow in untreated animals to an average volume of 36 cubic mm (FIG. 4a). As shown in FIG. 11b, both untreated animals and control animals treated with $PEI_{25}$-PEG-EGF+$PEI_2$-Mel carrier alone survived for an average of 32 days post-inoculation, whereas those treated with the dsRNA:carrier complex remained alive for at least 64 days post-inoculation while showing no signs of increased intracranial pressure.

Summary: The above described results demonstrate that: (i) glioblastoma tumors in-vivo are highly impermeable to penetration and infection by viral vectors; (ii) transfection and concomitant cell killing using dsRNA:carrier complex is at least 3 times more efficient using pIC:carrier complexes than using plasmid vectors; (iii) high apoptotic death rates of wild type EGFR overexpressing glioblastoma cells can be achieved 1 hour posttransfection with pIC:$PEI_{25}$-PEG-EGF complex; (iv) highly efficient and specific killing of EGFR overexpressing malignant glioma cells displaying wild type EGFR can be achieved by transfection with pIC:$PEI_{25}$-EGF-PEG complex; (v) incorporation of $PEI_2$-Mel carrier enhances cytotoxicity of pIC:$PEI_{25}$-PEG-EGF complex in wild type EGFR overexpressing target glioblastoma cells; (vi) EGFR overexpressing glioblastoma cells transfected with wild type pIC:$PEI_{25}$-PEG-EGF+$PEI_2$-Mel complex specifically secrete IFN-α and soluble growth inhibitory factors; and (vii) treatment with pIC:$PEI_{25}$-PEG-EGF+$PEI_2$-Mel complex can be used to cure mammals bearing lethal human wild type EGFR positive glioblastoma tumors.

Conclusion: The dsRNA:carrier complexes of the present invention can be used to kill in-vivo cells/tissue displaying a specific surface marker with optimal rapidity, efficacy, selectivity, and safety. Hence, the present invention is generally applicable for optimally treating relative to all prior art methods diseases associated with cells/tissue displaying a specific surface marker. The method of the present invention is particularly optimal relative to all prior art methods for treating diseases which are associated with highly impermeable tissues displaying a specific surface marker, such as glioblastoma muitiforme, the most malignant and lethal form of malignant glioma, due to the superior tissue penetration capacity of the dsRNA:carrier complexes of the present invention relative to viral vectors. By virtue of being generally applicable for killing cells/tissue displaying a specific marker, it will be appreciated that the method of the present invention is generally applicable for optimally treating numerous diseases associated with cells/tissue displaying a specific marker, including malignant, autoimmune, infectious, and transplantation-related diseases. It will also be particularly appreciated that by virtue of the exquisitely specific targeting achieved using the carriers of the present invention, that the method of the present invention can be used to treat diseases with minimal risk of harmful side-effects resulting from transfection of non-targeted cells.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, patent applications and sequences identified by their accession numbers mentioned in this specification are herein incorporated in their entirety by reference into the specification, to the same extent as if each individual publication, patent, patent application or sequence identified by its accession number was specifically and individually indicated to be incorporated herein by reference. In addition, citation or identification of any reference in this application shall not be construed as an admission that such reference is available as prior art to the present invention.

What is claimed is:

1. A method of killing malignant glioma cells over expressing epidermal growth factor receptors (EGFR), the method comprising exposing the malignant glioma cells to a composition-of-matter comprising:
   (i) a double stranded RNA molecule, said molecule consisting of 2 RNA strands which induces viral-like double stranded RNA mediated apoptosis, triggered by up-regulation of interferon (IFN)-α/-β expression in said cell and/or tissue;
   (ii) a nucleic acid carrier comprising polyethylenimine (PEI); and
   (iii) a targeting moiety comprising epidermal growth factor (EGF),
   wherein,
   said double stranded RNA molecule is associated with said nucleic acid carrier, said nucleic acid carrier is associated with said targeting moiety and said targeting moiety is not covalently bound to said double stranded RNA molecule, and further wherein said double stranded RNA, said targeting moiety and said nucleic acid carrier form a particle which penetrates solid tumor tissue, thereby killing the malignant glioma cells.

2. The method of claim 1, wherein said exposing the malignant glioma cells to said composition-of-matter is effected by administering said composition-of-matter to a vertebrate subject bearing the malignant glioma cells.

3. The method of claim 2, wherein said administering said composition-of-matter to said vertebrate subject is effected by administering said composition-of-matter to said subject systemically and/or to a central nervous system location of said vertebrate subject.

4. The method of claim 1, wherein said composition of matter further comprises melittin.

5. The method of claim 1, wherein said double stranded RNA molecule comprises a polyinosinic acid strand and/or a polycytidylic acid strand.

6. The method of claim 1, wherein said nucleic acid carrier further comprises poly(ethylene glycol).

7. The method of claim 1, wherein said double stranded RNA molecule is wholly composed of matching ribonucleotide pairs.

8. The method of claim 1, wherein said double stranded RNA molecule comprises mismatched ribonucleotide pairs on average less than one base pair in every 29 consecutive base residues.

9. The method of claim 4, wherein a ratio of said double stranded RNA molecule: said nucleic acid carrier: said melittin is selected such that at a concentration of 10 μg/ml the composition is capable of selectively killing more than 95% of glioblastoma cells 24 hours following transfection as measured in an in vitro assay.

10. The method of claim 1, wherein said carrier is covalently associated with said targeting moiety.

11. The method of claim 1, wherein said malignant glioma cells comprise glioblastoma cells.

* * * * *

```
SEQUENCE LISTING

<160> NUMBER OF SEQ ID NOS: 1

<210> SEQ ID NO 1
<211> LENGTH: 26
<212> TYPE: PRT
<213> ORGANISM: Artificial sequence
<220> FEATURE:
<223> OTHER INFORMATION: Melittin (Mel) peptide

<400> SEQUENCE: 1

Cys Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25
```